US008809258B2

(12) United States Patent
Kajihara et al.

(10) Patent No.: US 8,809,258 B2
(45) Date of Patent: Aug. 19, 2014

(54) METHOD FOR PRODUCING PEPTIDE

(75) Inventors: Yasuhiro Kajihara, Tokushima (JP);
Izumi Sakamoto, Tokushima (JP); Yuri Nambu, Tokushima (JP); Kazuhiro Fukae, Tokushima (JP); Hiroaki Asai, Tokushima (JP)

(73) Assignee: Glytech, Inc., Kyoto (JP)

( * ) Notice: Subject to any disclaimer, the term of this patent is extended or adjusted under 35 U.S.C. 154(b) by 1133 days.

(21) Appl. No.: 12/671,238

(22) PCT Filed: Jul. 30, 2008

(86) PCT No.: PCT/JP2008/063659
§ 371 (c)(1),
(2), (4) Date: Mar. 7, 2011

(87) PCT Pub. No.: WO2009/017154
PCT Pub. Date: Feb. 5, 2009

(65) Prior Publication Data
US 2011/0172392 A1 Jul. 14, 2011

(30) Foreign Application Priority Data
Jul. 31, 2007 (JP) ................................. 2007-199372

(51) Int. Cl.
A61K 38/00 (2006.01)
C07K 1/04 (2006.01)
C07K 14/00 (2006.01)

(52) U.S. Cl.
CPC ................. *C07K 1/04* (2013.01); *C07K 14/001* (2013.01)
USPC ........................................................ 514/1.1

(58) Field of Classification Search
CPC ................................ C07K 1/04; C07K 14/001
See application file for complete search history.

(56) References Cited

U.S. PATENT DOCUMENTS

| 5,958,496 A | 9/1999 | Amino et al. |
| 7,135,566 B2 | 11/2006 | Kajihara et al. |
| 7,273,934 B2 | 9/2007 | Kajihara et al. |
| 7,304,148 B2 | 12/2007 | Kajihara et al. |
| 2004/0181054 A1 | 9/2004 | Kajihara et al. |
| 2005/0222382 A1 | 10/2005 | Kajihara |
| 2006/0009421 A1 | 1/2006 | Kajihara et al. |
| 2006/0205039 A1 | 9/2006 | Fukae |
| 2006/0228784 A1 | 10/2006 | Kajihara et al. |
| 2007/0060543 A1 | 3/2007 | Kajihara et al. |
| 2008/0214798 A1 | 9/2008 | Kajihara et al. |
| 2009/0215100 A1 | 8/2009 | Kakehi et al. |
| 2009/0234095 A1 | 9/2009 | Kajihara |

FOREIGN PATENT DOCUMENTS

| WO | WO 96/34878 | 11/1996 |
| WO | WO 03/008431 A1 | 1/2003 |
| WO | WO 2004/005330 A1 | 1/2004 |
| WO | WO 2004/058824 A1 | 7/2004 |
| WO | WO 2004/058984 A1 | 7/2004 |
| WO | WO 2004/070046 A1 | 8/2004 |
| WO | WO 2005/010053 A1 | 2/2005 |
| WO | WO 2007/011055 A1 | 1/2007 |

OTHER PUBLICATIONS

Fan et al, Glycobiology, 2005, vol. 15, No. 10, pp. 952-964.*
Charpiot et al., Amino Acids, 1993, 5:421-453.*
Fan et al., Glycobiology, 2005, vol. 15, No. 10, pp. 952-964.*
Miller et al., Angew. Chem., 2003, 115, No. 4, 447-450.*
Dawson et al., Science, 1994, vol. 266, pp. 776-779.*
Vogt, Free Radical Biology & Medicine, 1995, vol. 18, No. 1, pp. 93-105.*
Perham et al., Amino Acids, Peptides, and Proteins, edited by G. T. Young, 1971, Chapter 2 by Perham et al., p. 45.*
Gross et al., Biochem. Biophys. Res. Comm. 1974, vol. 59, No. 3, 1145-1150, as in the IDS dated Nov. 11, 2011.*
Sohma et al., Chem. Commun., 2004, 124-125, also in the IDS dated Nov. 11, 2011.*
Shechter, J. Biolo. Chem., 1986, vol. 261, No. 1, 66-70.*
Clark, P.I. & Lowe, G., "Chemical Mutations of Papain. The preparation of Ser 25- and Gly 25-Papain"; *J.C.S. Chem. Comm.*, 1977, vol. 24, pp. 923-924.
Crich, D. & Banerjee, A.; "Native Chemical Ligation at Phenylalanine"; *J. Am. Chem. Soc.*, Jul. 21, 2007, vol. 129, No. 33, pp. 10064-10065.
Kajihara, Y., "Precise Chemical Synthesis of Glycopeptide"; *Bulletin of Yokohama City University, Natural Science 57*; Jan. 22, 2007; pp. 75-85. (English translation included).
Leplawy, T., et al., "α—Methylcysteine and its peptide chemistry"; *Amino Acids*, 1993, vol. 5, No. 3, p. 441.
Narayan, R.S., et al., "Versatile and Stereoselective Syntheses of Orthogonally Protected β-Methylcysteine and β-Methyllanthionine"; *Organic Letters*, 2005, vol. 7, No. 13, pp. 2655-2658.
Okamoto, R., et al., "Synthetic Study of Glyoprotein Having Single Structured Oligosaccharide"; *Yokohama City University, Graduate School*; Jul. 10, 2007; pp. 63. (English translation included).
Sasaoka, S. & Kajihara, Y., "Synthetic Study of Glycosylated Ovomucoid"; *Yokohama City University, Graduate School*; Mar. 2007, pp. 1231. (English translation included).

(Continued)

*Primary Examiner* — Marcela M Cordero Garcia
*Assistant Examiner* — Kaipeen Yang
(74) *Attorney, Agent, or Firm* — Brinks Gilson & Lione

(57) ABSTRACT

The present invention provides a method for producing a peptide, characterized in that it comprises converting an —SH group of a peptide comprising an amino acid residue having the —SH group to an —OH group, wherein said method comprises the following steps (a) to (c): (a) allowing an —SH group in a peptide to react with a methylating agent to convert the —SH group to an -SMe group; (b) allowing the -SMe group obtained in the step (a) to react with a cyanizing agent to produce a reaction intermediate; and (c) converting the reaction intermediate obtained in the step (b) to a peptide comprising an amino acid residue having an —OH group under more basic conditions than the conditions in the step (b).

12 Claims, No Drawings

(56) References Cited

OTHER PUBLICATIONS

Zhang, R., et al., "Probing the substrate specificity of Hepatitis C Virus NS3 serine protease by using synthetic peptides"; *J. Virol.*, 1997, vol. 71, No. 8, pp. 6208-6213.

Zhu, X., et al., "Synthesis of an S-linked glycopeptides analog derived from human Tamm-Horsfall glycoprotein"; *Org. Biomol. Chem.*, 2004, vol. 33, pp. 31-33.

Okamoto, Ryo et al., "*Uncovering a Latent Ligation Site for Glycopeptide Synthesis*", Angew. Chem. Int. Ed., 2008, vol. 47, pp. 5402-5406.

Yamamoto, Naoki et al., "*Chemical Synthesis of a Glycoprotein Having an Intact Human Complex-Type Sialyloligosaccharide under the Boc and Fmoc Synthetic Strategies*", J. Am. Chem. Soc., 2008, vol. 130, pp. 501-510.

Yamamoto, Naoki et al., "*An Approach for a Synthesis of Asparagine-Linked Sialylglycopeptides Having Intact and Homogeneous Complex-Type Undecadisialyloligosaccharides*", Chem. Eur. J., 2007, vol. 13, pp. 613-625.

Gross, Erhard et al., "*The Reaction of Cyanogen Bromide with S-Methylcysteine: Fragmentation of the Peptide 14-29 of Bovine Pancreatic Ribonuclease A*", Biochemical and Biophysical Research Communications, 1974, vol. 59, No. 3, pp. 1145-1150.

Sohma, Youhei et al., "*Novel and Efficient Synthesis of Difficult Sequence-Containing Peptides Through O-N Intramolecular Acyl Migration Reaction of O-acyl Isopeptides*", Chemm. Commun., 2004, pp. 124-1254.

Dekker, Jan et al., "*The MUC family: an obituary*", TRENDS in Biochemical Sciences, 2002, vol. 27, No. 3, pp. 126-131.

Singh, Ravibhushan et al., "*MUC1: A Target Molecule for Cancer Therapy*", Cancer Biology & Therapy, 2007, pp. 481-486.

Extended European Search Report for International Application No. PCT/JP2008063659 dated Oct. 10, 2011.

Biotechnology Journal, vol. 5-6, pp. 299-305 (2006).

Tateaki Wakamiya et al., "Synthesis of threo-3-Methylcysteine from Threonine," Bull. Chem. Soc. Jpn., vol. 55, pp. 3878-3881 (1982).

Japanese Office Action dated Nov. 5, 2013, Japanese App. No. 2009-525431.

* cited by examiner

METHOD FOR PRODUCING PEPTIDE

CROSS REFERENCE TO RELATED APPLICATIONS

This application claims the benefit of priority to PCT/JP2008/063659 filed Jul. 30, 2008, and JP 2007-199372 filed Jul. 31, 2007, the entire contents of which are each hereby incorporated herein by reference.

TECHNICAL FIELD

The present invention relates to a method for producing a peptide and a glycopeptide.

BACKGROUND

As a method for producing a peptide, a ligation method is useful. Among such ligation methods, a native chemical ligation method (NCL method) is a method capable of producing a peptide having a natural amide bond (peptide bond) at a ligation site. Such NCL method may be applied to two unprotected peptide chains. This method has been known as a method useful for forming a natural amide bond at a ligation site (for example, Patent Document 1). As shown in the figure below, the NCL method involves a chemical selective reaction between a first peptide having an α-carboxythioester portion at the C-terminus thereof and a second peptide having a cysteine residue at the N-terminus thereof. In this reaction, a thiol group (SH group, which may also be referred to as a sulfhydryl group) on the side chain of cysteine selectively reacts with a carbonyl carbon of a thioester group, and as a result of a thiol exchange reaction, a thioester-bound initial intermediate is generated. This intermediate intramolecularly rearranges on a voluntary basis to give a natural amide bond to a ligation site. At the same time, the intermediate regenerates thiol on the side chain of cysteine. Using this reaction, it became possible to efficiently synthesize various polypeptides.

Native Chemcial Ligation Method

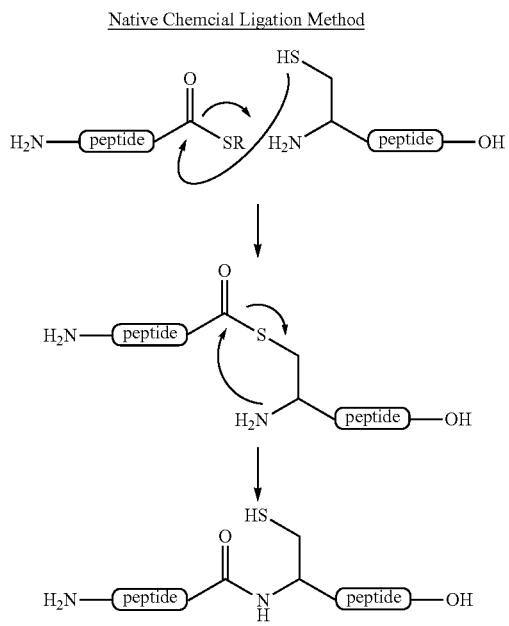

The main disadvantage of a typical NCL method is that either one of two peptide fragments to be ligated must have a cysteine residue at the N-terminus thereof, and that a peptide obtained after ligation also must have a cysteine residue at the ligation site in this method. Accordingly, in a case in which a desired peptide to be synthesized does not contain a cysteine residue, this method cannot be applied.

In addition, in a typical NCL method, two or more peptide fragments to be ligated are prepared by a solid-phase synthesis method, for example. When a peptide contains an extremely small amount of cysteine (or contains no cysteine), like a peptide existing in a living body, it has been necessary to prepare an extremely long peptide fragment to be subjected to such NCL method. Thus, it cannot be said that this is an efficient method.

On the other hand, it has been known that various glycopeptides and glycoproteins are present in a living body. The sugar chains of such glycopeptides or glycoproteins are broadly classified into two types; namely, N-linked sugar chains and O-linked sugar chains. N-linked sugar chain is generally a sugar chain binding to the nitrogen of amide on an asparagine side chain via an N-glycoside bond. In general, such N-linked sugar chain often binds to Asn in a consensus sequence -Asn-X-Ser/Thr- (wherein X represents an amino acid other than proline) in a natural state. O-linked sugar chain is a sugar chain binding to a hydroxyl group on a serine or threonine side chain via an O-glycoside bond. Examples of such N-linked and O-linked sugar chains will be given below (Gal: galactose; GlcNAc: N-acetylglucosamine; Man: mannose; Fuc: fucose; GalNAc: N-acetylgalactosamine). A natural glycopeptide having such O-linked sugar chain has been known to contain large amounts of proline, threonine, and serine (Non-Patent Documents 1 and 2).

Examples of N-linked sugar chain and O-linked sugar chain

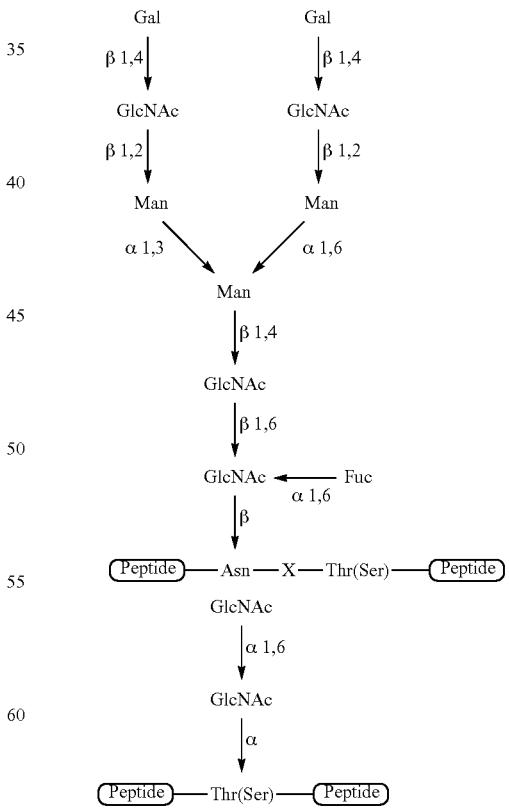

Patent Document 1: International Publication WO96/34878
Non-Patent Document 1: TRENDS in biochemical sciences, Vol. 27, No. 3, March 2002

Non-Patent Document 2: Cancer Biology & Therapy 6: 4, 481-486, April 2007

DISCLOSURE OF THE INVENTION

Technical Problem

It is an object of the present invention to provide a novel method for producing a peptide and a glycopeptide.

In particular, in a conventionally typical NCL method, either one of two peptide fragments to be ligated must have a cysteine residue at the N-terminus thereof, and further, a peptide obtained after ligation also must have a cysteine residue at the ligation site. Thus, the NCL method must have been designed and applied by using a cysteine residue of a desired peptide (or glycopeptide) to be finally obtained as a ligation site. Hence, the present invention provides a novel method for producing a peptide and a glycopeptide, which is able to design a ligation method, in which not only a cysteine residue in a desired peptide to be obtained, but also a portion corresponding to a serine residue or a threonine residue can be used as a ligation site.

More specifically, in one aspect of the present invention, a cysteine residue in a peptide (or a glycopeptide) can be converted to a serine residue. Thus, a peptide having a cysteine residue at the N-terminus thereof is ligated to another peptide according to the NCL method, and thereafter, this cysteine residue can be converted to a serine residue. Therefore, according to the present invention, even if a cysteine residue does not exist in a desired sequence to be obtained, if a serine residue exists therein, the position of the serine residue can be designed as a ligation site in the NCL method.

Moreover, in one aspect of the present invention, a peptide having, at the N-terminus thereof, a threonine derivative residue having an —SH group at the N-terminus thereof (or a threonine derivative residue having an —SH group that is protected by a disulfide bond or the like) is ligated to another peptide according to a ligation method, and thereafter, the obtained threonine derivative residue can be converted to a threonine residue. Therefore, according to the present invention, even if a cysteine residue does not exist in a desired sequence to be obtained, if a threonine residue exists therein, the position of the threonine residue can be designed as a ligation site in the ligation method.

Thus, the present invention provides a novel method for producing a peptide and a glycopeptide using a ligation method, wherein serine or threonine that is abundant in glycopeptides can be designed as a ligation site in the ligation method.

Solution to Problem

In order to solve the aforementioned problems, the present invention may have the following characteristics.

The present invention may provide a method for producing a peptide, characterized in that it comprises converting an —SH group of a peptide comprising an amino acid residue having the —SH group to an —OH group, wherein said method comprises the following steps (a) to (c):

(a) allowing an —SH group in a peptide to react with a methylating agent;

(b) allowing an -SMe group obtained in the step (a) to react with a cyanizing agent; and (c) modifying the reaction conditions to become more basic than the conditions in the step (b).

The present invention may also provide a method for producing a peptide, characterized in that it comprises converting an —SH group of a peptide comprising an amino acid residue having the —SH group to an —OH group, wherein said method comprises the following steps (a) to (c):

(a) allowing an —SH group in a peptide to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a peptide comprising an amino acid residue having an —OH group under more basic conditions than the conditions in the step (b).

The present invention may also provide a method for producing a peptide, characterized in that it comprises converting a cysteine residue of a peptide comprising the cysteine residue to a serine residue, wherein said method comprises the following steps (a) to (c):

(a) allowing an —SH group of a cysteine residue in a peptide to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a peptide comprising a serine residue under more basic conditions than the conditions in the step (b).

The present invention may also provide a method for producing a peptide, characterized in that it comprises converting a threonine derivative A residue represented by the following Formula (1) of a peptide comprising the threonine derivative A residue as an amino acid residue to a threonine residue,

(1)

wherein said method comprises the following steps (a) to (c):

(a) allowing an —SH group of a threonine derivative A residue in a peptide to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a peptide comprising a threonine residue under more basic conditions than the conditions in the step (b).

The present invention may also provide a method for producing a peptide, characterized in that it comprises converting an -SMe group of a peptide comprising an amino acid residue having the -SMe group to an —OH group, wherein said method comprises the following steps (b) and (c):

(b) allowing an -SMe group in a peptide to react with a cyanizing agent to produce a reaction intermediate; and (c) converting the reaction intermediate obtained in the step (b) to a peptide comprising an amino acid residue having an —OH group under more basic conditions than the conditions in the step (b).

The present invention may also provide a method for producing a peptide comprising an amino acid residue having an —OH group, which comprises the following steps:

(o) ligating a first peptide containing, at the C-terminus thereof, an amino acid residue in which a carboxyl group is substituted with an α-carboxythioester group represented by the formula —C(═O)—SR (wherein R is selected from a benzyl group, an aryl group, and an alkyl group, which may be substituted with substituents), to a second peptide containing, at the N-terminus thereof, an amino acid residue having an —SH group according to a ligation method to obtain a peptide comprising an amino acid residue having an —SH group;

(a) allowing the —SH group in the peptide obtained in the step (o) to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a peptide comprising an amino acid residue having an —OH group under more basic conditions than the conditions in the step (b).

The present invention may also provide a method for producing a peptide comprising a serine residue, which comprises the following steps:

(o) ligating a first peptide containing, at the C-terminus thereof, an amino acid residue in which a carboxyl group is substituted with an α-carboxythioester group represented by the formula —C(=O)—SR (wherein R is selected from a benzyl group, an aryl group, and an alkyl group, which may be substituted with substituents), to a second peptide containing, at the N-terminus thereof, a cysteine residue according to a ligation method to obtain a peptide comprising a cysteine residue;

(a) allowing an —SH group of the cysteine residue in the peptide obtained in the step (o) to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a peptide comprising a serine residue under more basic conditions than the conditions in the step (b).

The present invention may also provide a method for producing a peptide comprising a threonine residue, which comprises the following steps:

(o) ligating a first peptide containing, at the C-terminus thereof, an amino acid residue in which a carboxyl group is substituted with an α-carboxythioester group represented by the formula —C(=O)—SR (wherein R is selected from a benzyl group, an aryl group, and an alkyl group, which may be substituted with substituents), to a second peptide containing, at the N-terminus thereof, a threonine derivative residue according to a ligation method to obtain a peptide comprising a threonine derivative A represented by the aforementioned Formula (1) as an amino acid residue;

(a) allowing an —SH group of the threonine derivative A residue in the peptide obtained in the step (o) to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a peptide comprising a threonine residue under more basic conditions than the conditions in the step (b).

The present invention may also provide a method for producing a glycopeptide, characterized in that it comprises converting an —SH group of a glycopeptide comprising an amino acid residue having the —SH group to an —OH group, wherein said method comprises the following steps (a) to (c):

(a) allowing an —SH group in a glycopeptide to react with a methylating agent;

(b) allowing an -SMe group obtained in the step (a) to react with a cyanizing agent; and (c) modifying the reaction conditions to become more basic than the conditions in the step (b).

The present invention may also provide a method for producing a glycopeptide, characterized in that it comprises converting an —SH group of a glycopeptide comprising an amino acid residue having the —SH group to an —OH group, wherein said method comprises the following steps (a) to (c):

(a) allowing an —SH group in a glycopeptide to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a glycopeptide comprising an amino acid residue having an —OH group under more basic conditions than the conditions in the step (b).

The present invention may also provide a method for producing a glycopeptide, characterized in that it comprises converting a cysteine residue of a glycopeptide comprising the cysteine residue to a serine residue, wherein said method comprises the following steps (a) to (c):

(a) allowing an —SH group of a cysteine residue in a glycopeptide to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a glycopeptide comprising a serine residue under more basic conditions than the conditions in the step (b).

The present invention may also provide a method for producing a glycopeptide, characterized in that it comprises converting a threonine derivative A residue represented by the aforementioned Formula (1) of a glycopeptide comprising the threonine derivative A residue as an amino acid residue to a threonine residue, wherein said method comprises the following steps (a) to (c):

(a) allowing an —SH group of a threonine derivative A residue in a glycopeptide to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a glycopeptide comprising a threonine residue under more basic conditions than the conditions in the step (b).

The present invention may also provide a method for producing a glycopeptide comprising an amino acid residue having an —OH group, which comprises the following steps:

(o) ligating a first peptide or glycopeptide containing, at the C-terminus thereof, an amino acid residue in which a carboxyl group is substituted with an α-carboxythioester group represented by the formula —C(=O)—SR (wherein R is selected from a benzyl group, an aryl group, and an alkyl group, which may be substituted with substituents), to a second peptide or glycopeptide containing, at the N-terminus thereof, an amino acid residue having an —SH group according to a ligation method, provided that at least one of the first peptide or glycopeptide and a second peptide or glycopeptide is a glycopeptide to obtain a glycopeptide comprising an amino acid residue having an —SH group;

(a) allowing the —SH group in the glycopeptide obtained in the step (o) to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a glycopeptide comprising an amino acid residue having an —OH group under more basic conditions than the conditions in the step (b).

The present invention may also provide a method for producing a glycopeptide comprising a serine residue, which comprises the following steps:

(o) ligating a first glycopeptide whose C-terminus is represented by the following formula:

-sugar Asn-X—C(=O)—SR (wherein sugar Asn represents a sugar chain-added asparagine, X represents a portion other than a carboxyl group of any given amino acid residue other than proline, and R is selected from a benzyl group, an aryl group, and an alkyl group, which may be substituted with substituents), to a second peptide containing a cysteine residue at the N-terminus thereof according to a ligation method to obtain a glycopeptide containing a cysteine residue;

(a) allowing an —SH group of the cysteine residue in the glycopeptide obtained in the step (o) to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a glycopeptide comprising a serine residue under more basic conditions than the conditions in the step (b).

The present invention may also provide a method for producing a glycopeptide comprising a threonine residue, which comprises the following steps:

(o) ligating a first glycopeptide whose C-terminus is represented by the following formula:

-sugar Asn-X—C(=O)—SR (wherein sugar Asn represents a sugar chain-added asparagine, X represents a portion other than a carboxyl group of any given amino acid residue other than proline, and R is selected from a benzyl group, an aryl group, and an alkyl group, which may be substituted with substituents), to a second peptide containing a threonine derivative residue at the N-terminus thereof according to a ligation method to obtain a glycopeptide containing a threonine derivative A represented by the aforementioned Formula (1) as an amino acid residue;

(a) allowing an —SH group of the threonine derivative A residue in the glycopeptide obtained in the step (o) to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a glycopeptide comprising a threonine residue under more basic conditions than the conditions in the step (b).

The present invention may also provide a glycopeptide having a structure represented by the following formula:

-sugar Asn-X—Y— wherein sugar Asn represents a sugar chain-added asparagine,

X represents any given amino acid residue other than proline, and

Y represents a threonine derivative A residue represented by Formula (2):

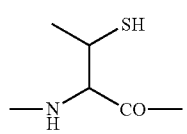

(2)

In one embodiment of the present invention, the methionine residue in the peptide or glycopeptide in the step (a) or step (o) may preferably be a protected methionine residue, and in which the production method preferably further comprises the following step (d), after the step (b) or (c), and particularly after the step (c), as desired:

(d) deprotecting the protected methionine residue.

In one embodiment of the present invention, the reaction intermediate obtained in the step (b) may preferably be an ester form.

In one embodiment of the present invention, the step (b) may preferably be carried out under acidic conditions, and particularly at pH 2 to 3.

In one embodiment of the present invention, the cyanizing agent used in the step (b) is preferably cyanogen bromide.

In one embodiment of the present invention, the step (c) may preferably be carried out under weakly basic conditions, for example, at pH 7 to 9, and particularly at pH 7 to 8. When the step (c) is carried out under weakly basic conditions, in one embodiment, the step (c) may preferably be carried out for approximately 10 minutes or more, and particularly for approximately 15 minutes or more (for example, for approximately 10 minutes to 30 hours, and particularly for approximately 15 minutes to 30 hours).

In one embodiment of the present invention, the step (c) may preferably be carried out under strongly basic conditions, for example, at pH 9 to 13, and particularly at pH 10 to 11. When the step (c) is carried out under strongly basic conditions, in one embodiment, the step (c) may preferably be carried out for approximately 1 hour or less, and particularly for approximately 10 minutes or less (for example, for approximately 5 minutes to 1 hour, and particularly for approximately 5 minutes to 10 minutes).

In one embodiment of the present invention, when a threonine derivative residue is contained at the N-terminus of the second peptide, the aforementioned threonine derivative residue may be an N-terminal amino acid residue of a threonine derivative represented by the following Formula (3):

(3)

(wherein R represents H or a protecting group for a thiol group that is easily deprotected under conditions of a ligation reaction, and such R preferably represents H or a disulfide group).

In one embodiment of the present invention, either one of, or more specifically both of, the first peptide (or glycopeptide) and the second peptide (or glycopeptide) preferably may not contain cysteine, or contain protected cysteine.

In one embodiment of the present invention, either the first peptide (or glycopeptide) or the second peptide (or glycopeptide) may preferably be a peptide (or a glycopeptide) having 80 or less, preferably 50 or less, and more preferably 30 or less amino acid residues.

In one embodiment of the present invention, a sugar chain in a glycopeptide may preferably be an N-linked sugar chain or an O-linked sugar chain.

In one embodiment of the present invention, the sugar chain represented by the following Formula (4) may be preferable as a sugar chain.

(4)

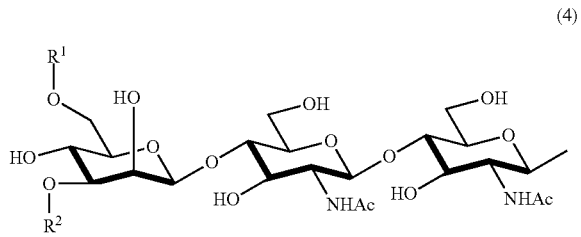

[wherein each of $R^1$ and $R^2$ independently represents a hydrogen atom or a group represented by each of Formulas (5) to (8)].

(5)

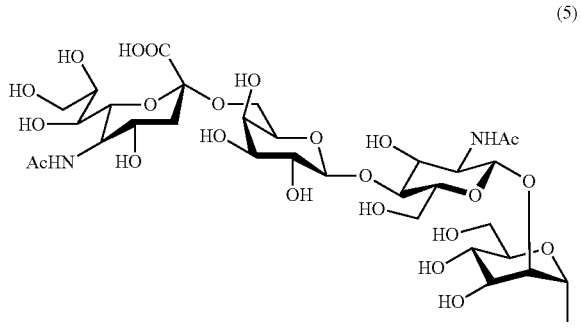

(6)

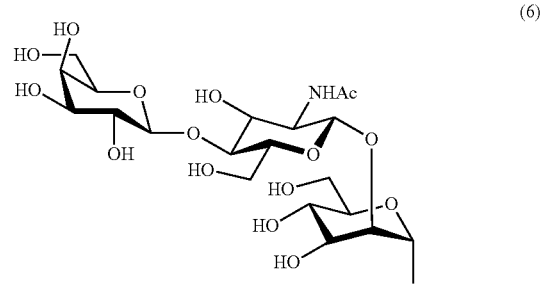

(7)

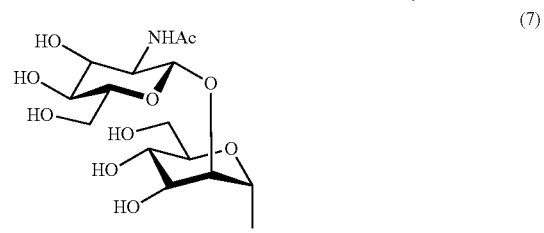

(8)

In one embodiment of the present invention, the production method may preferably further comprise a step of adding a sugar chain after the step (c) or the step (d).

In one embodiment, all amide bonds in the peptide or glycopeptide obtained by the production method of the present invention may preferably be natural amide bonds.

In one embodiment, all constitutive amino acids of the peptide or glycopeptide obtained by the production method of the present invention may preferably be amino acids existing as constitutive amino acids of a peptide or glycopeptide in a living body.

Advantageous Effects of Invention

According to the method for producing a peptide of the present invention, an —SH group of a peptide having such —SH group can be converted to an —OH group. In addition, an —SH group of a peptide comprising an amino acid residue having such —SH group, which is obtained by ligating a first peptide having an α-carboxythioester portion represented by —C(=O)—SR at the C-terminus thereof to a second peptide comprising an amino acid residue having an —SH group at the N-terminus thereof according to a ligation method, can be converted to an —OH group. These methods can also be applied to glycopeptides.

Thus, according to the method for producing a peptide of the present invention, a cysteine residue in a peptide can be converted to a serine residue. As a result, even if a cysteine residue does not exist in a desired sequence to be obtained, if a serine residue exists therein, the NCL method can be applied.

Moreover, the present invention also provides a ligation method in which a threonine derivative having an —SH group is used as a ligation site. Since a threonine derivative residue having an —SH group in a peptide obtained by this ligation method can be converted to a threonine residue, it becomes possible to apply a ligation method using a threonine residue as a ligation site to the production of a peptide having threonine.

Cysteine, which has been used as a ligation site in the conventional native chemical ligation method, is contained in a small amount in a peptide existing in a living body. According to the method of the present invention, serine and threonine, which are contained in large amounts in a peptide, and particularly, in a glycopeptide existing in a living body, can be designed as new ligation sites in a ligation method.

Furthermore, the aforementioned method is applied to a glycopeptide, and particularly, to a glycopeptide having an O-linked sugar chain containing large amounts of serine and threonine, or a glycopeptide having an N-linked sugar chain having, as a consensus sequence, the sequence -sugar Asn-X-Ser- or -sugar Asn-X-Thr (wherein the sugar Asn represents a sugar chain-added asparagine, and X represents any given amino acid residue other than proline) to produce, utilizing a ligation method, a glycopeptide having an N-linked sugar chain or an O-linked sugar chain, which has the same structure as that of a natural glycopeptide.

BEST MODE FOR CARRYING OUT THE INVENTION

In a first aspect, the present invention relates to subjecting a peptide comprising an amino acid residue having an —SH group to the following steps (a) to (c) to obtain a peptide comprising an amino acid residue having an —OH group:

(a) allowing an —SH group in a peptide to react with a methylating agent;

(b) allowing an -SMe group obtained in the step (a) to react with a cyanizing agent; and (c) modifying the reaction conditions to become more basic than the conditions in the step (b).

The above described steps (a) to (c) are more specifically the following steps:

(a) allowing an —SH group in a peptide to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a peptide comprising an amino acid residue having an —OH group under more basic conditions than the conditions in the step (b).

In a second aspect, the present invention relates to performing the following steps:

ligating a first peptide containing, at the C-terminus thereof, an amino acid residue in which a carboxyl group is substituted with an α-carboxythioester group represented by the formula —C(═O)—SR (wherein R is selected from a benzyl group, an aryl group, and an alkyl group, which may be substituted with substituents), to a second peptide containing, at the N-terminus thereof, an amino acid residue having an —SH group according to a ligation method to obtain a peptide comprising an amino acid residue having an —SH group; and steps including the above described steps (a) to (c) to obtain a peptide comprising an amino acid residue having an —OH group.

In a third aspect, the present invention relates to subjecting a glycopeptide comprising an amino acid residue having an —SH group to steps including the above described steps (a) to (c) to obtain a glycopeptide comprising an amino acid residue having an —OH group.

In a fourth aspect, the present invention relates to performing the following steps:

ligating a first glycopeptide whose C-terminus is represented by the following formula:

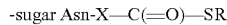

-sugar Asn-X—C(═O)—SR (wherein sugar Asn represents a sugar chain-added asparagine, X represents a portion other than a carboxyl group of any given amino acid residue other than proline, and R is selected from a benzyl group, an aryl group, and an alkyl group, which may be substituted with substituents), to a second peptide comprising an amino acid residue having an —SH group at the N-terminus thereof according to a ligation method to obtain a glycopeptide comprising an amino acid residue having an —SH group; and steps including the above described steps (a) to (c) to obtain a glycopeptide comprising an amino acid residue having an —OH group.

In the present specification, the "peptide" is not particularly limited, as long as two or more amino acids bind to one another via an amide bond therein. Thus, the term "peptide" is used herein to include a known peptide, a novel peptide, and a modified peptide form. In the present invention, those generally referred to as proteins are also included in such peptide. In a preferred aspect, in a peptide (or a glycopeptide) obtained by the production method of the present invention, two or more amino acids bind to one another via the same amide bond (peptide bond) as that of a natural peptide or glycopeptide.

In the present specification, the term "modified peptide form" is used to mean a compound obtained by naturally or artificially modifying a peptide. Examples of such modification include alkylation, acylation (for example, acetylation), amidation (for example, amidation of the C-terminus of a peptide), carboxylation, esterification, the formation of a disulfide bond, glycosylation, lipidation, phosphorylation, hydroxylation, and the binding of a labeling substance, all of which are performed on one or multiple amino acid residues of a peptide.

In the present specification, the term "amino acid" is used in the broadest sense. Thus, in the present specification, the term "amino acid" includes not only natural amino acids such as serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gin), threonine (Thr), cysteine (Cys), methionine (Met), phenylalanine (Phe), tryptophan (Trp) and proline (Pro), but also non-natural amino acids such as amino acid mutants and derivatives. Taking into consideration such broad definitions, persons skilled in the art could understand that the amino acid in the present specification includes, for example: L-amino acids; D-amino acids; chemically modified amino acids such as amino acid mutants and derivatives; amino acids that do not become constituent materials for proteins in a living body, such as norleucine, β-alanine, and ornithine; and chemically synthesized compounds having amino acid properties known to persons skilled in the art. Examples of a non-natural amino acid include α-methylamino acids (α-methylalanine, etc.), D-amino acids, histidine-like amino acids (2-amino-histidine, β-hydroxy-histidine, homohistidine, α-fluoromethyl-histidine, α-methyl-histidine, etc.), amino acids having excessive methylene on their side chain ("homo" amino acids), amino acids whose carboxylic acid functional group in the side chain is substituted with a sulfonic acid group (cysteic acid, etc.), as well as a threonine derivative A as described in detail below.

In the present specification, the term "threonine derivative" is used to mean a compound represented by the following Formula (3):

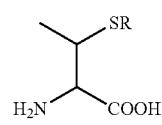

(3)

In Formula (3), R represents H or a protecting group for a thiol group that is easily deprotected under conditions of a ligation reaction, and such R preferably represents H or a disulfide group. In particular, a compound represented by the following Formula (1), wherein R is H in the above Formula (3), is referred to as a threonine derivative A.

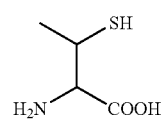

(1)

The threonine derivative of Formula (3) is a compound in which an —OH group portion of threonine is an —SH group. Such threonine derivative includes those having all types of configurations. In the production method of the present invention, it is considered that space inversion takes place when an —SH group of an amino acid residue in a peptide is converted to an —OH group. Thus, particularly when threonine existing in the nature is to be obtained, a threonine derivative having an —SR group whose configuration is inverted with respect to an —OH group of threonine existing in the nature may preferably be used.

The aforementioned threonine derivative can be obtained by the following method, referring to the examples and the synthesis examples as described later, for instance.

First, threonine comprising an amino group and a carboxyl group that have been protected is prepared. The types of such protecting groups are not particularly limited, as long as a peptide of interest can be obtained in the subsequent reaction. For example, threonine with an amino group protected by a Boc group and a carboxyl group protected by TMSE (trimethylsilylethyl) group can be used. Thereafter, the hydroxyl group at J3-position is mesylated by a known method. Subsequently, using DBU and thioacetic acid, for example, this mesyl group is substituted into a thioacetyl group (see D. Crich et al, J. Am. Chem. Soc., 129, 10064 (2007)).

According to a known method, this thioacetyl group is converted to a thiol group protected by a protecting group known to persons skilled in the art, such as a disulfide group, an acetamidemethyl group, a nitrobenzyl group, or a trityl group. For example, when the thioacetyl group is converted to a thiol group protected by a disulfide group, Synthesis Example 1 as described later can be used as a reference. The disulfide group is easily deprotected under the reaction conditions for the subsequent ligation method.

In a preferred aspect, the peptide (or glycopeptide) obtained by the production method of the present invention consists of amino acids that are all present as constitutive amino acids of the peptide (or glycopeptide) in a living body. In addition, in one aspect of the present invention, the peptide obtained by the production method of the present invention is preferably a peptide that does not contain a cysteine residue or contains small quantities of cysteine residues in the constitutive amino acids. Moreover, in one aspect of the present invention, the peptide obtained by the production method of the present invention has 80 or less, preferably 50 or less, and more preferably 30 or less amino acid residues between any given serine residue or threonine residue and the next serine residue or threonine residue, or the N-terminus or the C-terminus. For instance, in one aspect of the present invention, the peptide obtained by the production method of the present invention has one or more serine residues or threonine residues in 5 to 40 amino acid residues, and preferably in 20 to 30 amino acid residues.

In the present specification, the term "reaction intermediate" is used to mean all compounds produced in the period between the reaction of an -SMe group in a peptide with a cyanizing agent and the subsequent conversion of the -SMe group to an —OH group, in a broad sense. The reaction scheme of the present invention is considered to be the following scheme 1. In the scheme 1, the ester form represented by C is also a reaction intermediate in the present invention. The present specification contains the description "peptide-OH" in the following scheme 1, for example. Such "—OH" means the —OH of the C-terminal carboxyl group of the peptide, unless otherwise specified.

Scheme 1

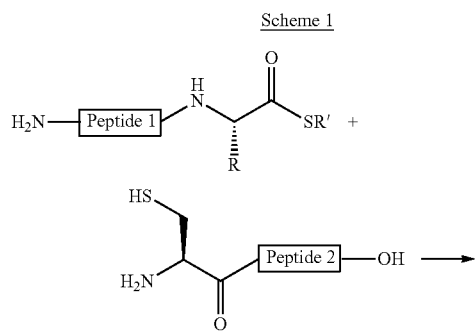

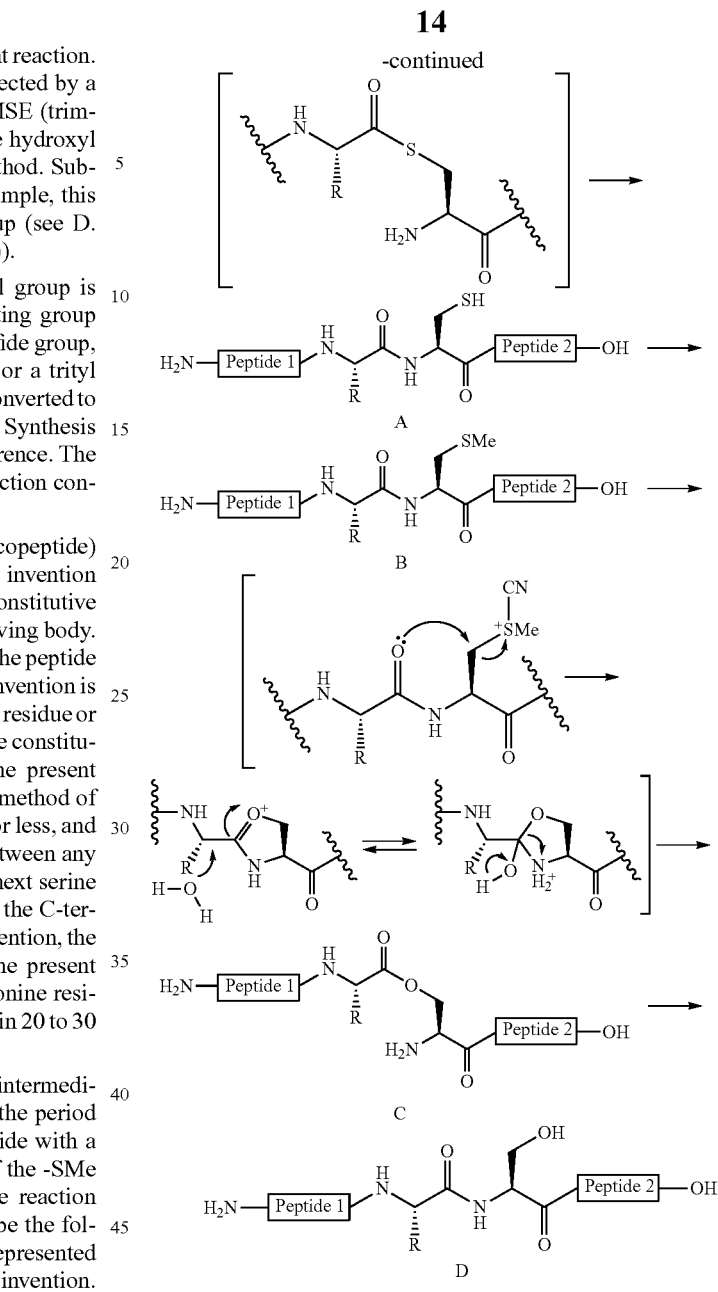

In the present specification, the term "glycopeptide" is not particularly limited, as long as it is a compound formed by adding at least one sugar chain to the aforementioned peptide. The glycopeptide includes known glycopeptides and novel glycopeptides. Those generally referred to as glycoproteins are also included in the glycopeptide of the present invention.

In a preferred aspect, the glycopeptide obtained by the production method of the present invention is a peptide having an N-linked sugar chain or an O-linked sugar chain. Examples of such glycopeptide include a part or all of peptides such as erythropoietin, interleukin, interferon-13, an antibody, and a monocyte chemotactic factor protein-3(MCP-3).

In one aspect of the present invention, the glycopeptide obtained by the production method of the present invention has 80 or less, preferably 50 or less, and more preferably 30 or less amino acid residues between any given serine residue or threonine residue to which the sugar chain is not added and the next serine residue or threonine residue, or the N-terminus or the C-terminus to which the sugar chain is not added. For instance, in one aspect of the present invention, the glycopeptide obtained by the production method of the present invention has one or more serine residues or threonine residues in 5 to 40 amino acid residues, and preferably in 20 to 30 amino acid residues.

In the case of such glycopeptide, a sugar chain may bind to an amino acid residue in the peptide, directly or via a linker. The binding site of a sugar chain and an amino acid is not particularly limited. An amino acid preferably binds to the reducing terminus of a sugar chain.

The type of an amino acid to which a sugar chain binds is not particularly limited. A sugar chain may bind to either a natural amino acid or a non-natural amino acid. From the viewpoint that the present glycopeptide should have a structure identical to or similar to that of a glycopeptide (glycoprotein) existing in a living body, a sugar chain preferably binds to Asn as in the case of an N-linked sugar chain, or to Ser or Thr as in the case of an O-linked sugar chain. In particular, in the case of an N-linked sugar chain, the glycopeptide obtained by the production method of the present invention preferably has a structure (-sugar Asn-X-Thr/Ser-) in which a sugar chain binds to Asn, an amino acid (X) other than proline binds to the C-terminal side of the Asn via an amide bond (peptide bond), and further, Thr or Ser binds to the C-terminal side of the X via an amide bond (peptide bond).

When a sugar chain binds to an amino acid via a linker, from the viewpoint of the property of easily binding to the linker, preferred amino acids to which the sugar chain binds include: an amino acid having two or more carboxyl groups in its molecule, such as aspartic acid or glutamic acid; an amino acid having two or more amino groups in its molecule, such as lysine, arginine, histidine, or tryptophan; an amino acid having a hydroxyl group in its molecule, such as serine, threonine, or tyrosine; an amino acid having a thiol group in its molecule, such as cysteine; and an amino acid having an amide group in its molecule, such as asparagine or glutamine. In particular, from the viewpoint of reactivity, aspartic acid, glutamic acid, lysine, arginine, serine, threonine, cysteine, asparagine, and glutamine are preferable.

In a case in which a sugar chain binds to an amino acid via a linker in a glycopeptide, linkers that have been widely used in the present field can be used herein as linkers. Examples of such linker include:

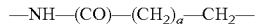

—NH—(CO)—(CH$_2$)$_a$—CH$_2$—

(wherein a is an integer, which is not particularly limited unless it interferes a linker function of interest, and is preferably an integer from 0 to 4); C$_{1-10}$ polymethylene; and

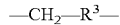

—CH$_2$—R$^3$—

(wherein R$^3$ represents a group produced by dissociating a single hydrogen atom from a group selected from the group consisting of alkyl, substituted alkyl, alkenyl, substituted alkenyl, alkynyl, substituted alkynyl, aryl, substituted aryl, a carbocyclic group, a substituted carbocyclic group, a heterocyclic group, and a substituted heterocyclic group).

In the present specification, the term "sugar chain" includes not only a compound formed by connecting two or more unit sugars (monosaccharides and/or the derivatives thereof), but also a compound consisting of a single unit sugar (a monosaccharide and/or the derivative thereof). Examples of such sugar chain include a wide range of sugar chains including: monosaccharides and polysaccharides contained in a living body (glucose, galactose, mannose, fucose, xylose, N-acetylglucosamine, N-acetylgalactosamine, sialic acid, and the complex and derivative thereof); and sugar chains decomposed or induced from complex biomolecules such as a decomposed polysaccharide, a glycoprotein, a proteoglycan, a glycosaminoglycan, and a glycolipid. However, examples are not limited thereto. When two or more unit sugars are connected with one another, a unit sugar binds to another unit sugar due to dehydration condensation due to a glycoside bond. A sugar chain may be of either a linear type or a branched type.

Moreover, in the present specification, sugar chain derivatives are also included in the "sugar chain." Examples of such sugar chain derivative include: a sugar constituting a sugar chain, which has a carboxyl group (for example, aldonic acid whose position C-1 has been oxidized to carboxylic acid (e.g. D-gluconic acid obtainable by oxidizing D-glucose), and uronic acid, the C atom at the terminus of which has been converted to carboxylic acid (D-glucuronic acid obtainable by oxidizing D-glucose)); a sugar having an amino group or a derivative thereof (e.g. an acetylated amino group) (for example, N-acetyl-D-glucosamine, N-acetyl-D-galactosamine, etc.); a sugar having both an amino group and a carboxyl group (for example, N-acetylneuraminic acid (sialic acid), N-acetyl muramic acid, etc.); a deoxy sugar (for example, 2-deoxy-D-ribose); a sulfated sugar containing a sulfate group; and a phosphorylated sugar containing a phosphate group. However, examples are not limited thereto.

The sugar chain of the present invention is preferably a sugar chain that exists as a complex carbohydrate in a living body (a glycopeptide (or a glycoprotein), a proteoglycan, a glycolipid, etc.). The present sugar chain is preferably an N-linked sugar chain, an O-linked sugar chain, or the like, which binds as a glycopeptide (or a glycoprotein) to a peptide (or a protein) in a living body. In an O-linked sugar chain-binding glycopeptide, N-acetylgalactosamine (GalNAc), N-acetylglucosamine (GlcNAc), xylose, fucose, and the like bind to the Ser or Thr of a peptide via an O-glycoside bond, and a sugar chain is further added to such bound body. Examples of an N-linked sugar chain include a high mannose type, a complex type, and a hybrid type. Of these, a complex type is preferable.

In the present invention, a preferred sugar chain is the sugar chain represented by the following Formula (4), for example:

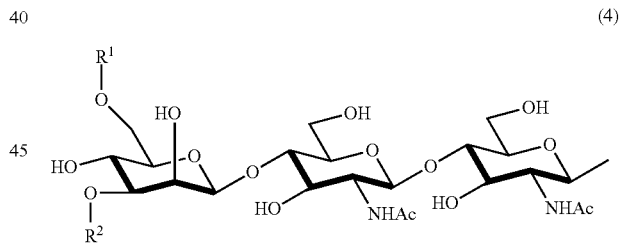

(4)

[wherein each of R$^1$ and R$^2$ independently represents a hydrogen atom or a group represented by each of Formulas (5) to (8)].

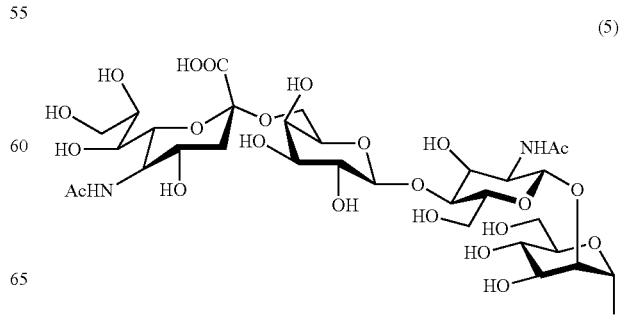

(5)

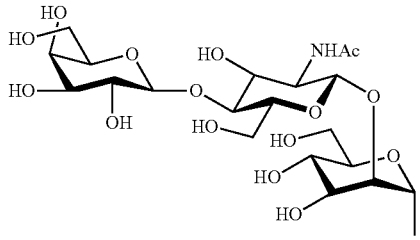

(6)

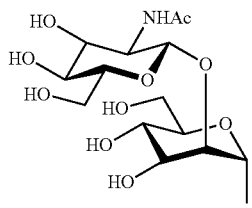

(7)

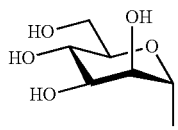

(8)

In order to prevent problems, such as antigenicity, which may occur when the method for producing a glycopeptide of the present invention is applied to the field of production of pharmaceutical products and the like, examples of a preferred sugar chain used include: a sugar chain having a structure identical to that of a sugar chain existing as a glycoprotein that binds to a protein in a human body (having the same types of constituent sugars and the same binding manners) (for example, the sugar chain described in FEBS LETTERS Vol. 50, No. 3, February 1975); and a sugar chain formed by losing one or multiple sugars from the non-reducing terminus of the aforementioned sugar chain.

The number of sugar chains added to a glycopeptide is not particularly limited, as long as it is 1 or greater. From the viewpoint of the production of a glycopeptide having a structure similar to that of a glycopeptide existing in a living body, the number of sugar chains added is more preferably almost the same as that of a glycopeptide existing in a body.

In a preferred aspect of the present invention, the structures of sugar chains in the glycopeptides of the present invention are uniform. In the present specification, such expression as "the structures of sugar chains in the glycopeptides are uniform" means that, when a comparison is made between glycopeptides, the sites of addition of sugar chains, the types of sugars constituting sugar chains, a binding order, and a sugar binding manner are identical between them, and that the structures of sugar chains are uniform at a percentage of at least 90% or more, preferably 95% or more, and more preferably 99% or more. Glycopeptides having uniform sugar chains are of the same quality, and such glycopeptides are preferably used, in particular, in the field of the production of pharmaceutical products, assay, and the like.

A peptide used as a raw material in the production method of the present invention can be produced by applying peptide production methods known to persons skilled in the art, such as solid-phase synthesis, liquid-phase synthesis, synthesis using cells, and a method of separating and extracting naturally-occurring products. In addition, when a glycopeptide is used as a raw material, such glycopeptide can be produced by incorporating a step of adding sugar chains into the aforementioned known peptide production methods. With regard to a method for producing sugar chains used in such sugar chain-adding step, International Publications WO03/008431, WO2004/058984, WO2004/058824, WO2004/070046, WO2007/011055, etc. can be referred.

As a specific example, a method for producing a peptide or a glycopeptide comprising an amino acid residue having an —SH group according to a solid-phase synthesis method will be described below. As for the below-mentioned method, International Publication WO2004/005330 can also be referred.

First, (1) a hydroxyl group of a resin having a hydroxyl group and a carboxyl group of an amino acid whose amino group is protected by a fat-soluble protecting group are subjected to an esterification reaction. In this case, since the amino group of the amino acid is protected by the fat-soluble protecting group, the self-condensation of amino acids is prevented, and the hydroxyl group of the resin reacts with the carboxyl group of the amino acid, so that esterification takes place.

Next, (2) the fat-soluble protecting group of the ester as obtained above is dissociated to form a free amino group, (3) this free amino group is amidated with a carboxyl group of a desired amino acid whose amino group is protected by a fat-soluble protecting group, (4) the aforementioned fat-soluble protecting group is dissociated to form a free amino group, and (5) the aforementioned steps (3) and (4) are repeated as necessary to obtain a peptide in which a desired number of desired amino acids are ligated, and which has a resin at one terminus thereof and also has a free amino group at another terminus thereof.

Using an amino acid having an —SH group (wherein the —SH group may be protected) (for example, cysteine or the aforementioned threonine derivative of Formula (3)) in the aforementioned steps (1) to (5), a peptide comprising an amino acid residue having an —SH group can be obtained. When an —SH group of an amino acid having the —SH group is used in the aforementioned steps (1) to (5), the —SH group may be protected by a protecting group known to persons skilled in the art, such as a disulfide group, an acetamidemethyl group, a nitrobenzyl group, or a trityl group. Thereafter, such protecting group is removed, as necessary. Moreover, using a sugar chain-added amino acid (for example, sugar chain asparagine formed by adding a sugar chain to asparagine, sugar chain serine or sugar chain threonine formed by adding a sugar chain to serine or threonine, and the like) as an amino acid in the aforementioned steps (1) to (5), N-linked and/or O-linked glycopeptides having one or two or more sugar chains at a desired position(s) can also be obtained. As described above, such N-linked and/or O-linked glycopeptides are able to comprise an amino acid residue(s) having an —SH group(s) at a desired position(s).

(6) Thereafter, the ester bond between the resin and the amino acid in (1) above is cleaved by an acid to produce a desired peptide (or glycopeptide).

Generally, the type of a solid-phase resin is not particularly limited, as long as it is a resin used in solid-phase synthesis. For instance, Amino-PEGA resin (manufactured by Merck), Wang resin (manufactured by Merck), HMPA-PEGA resin (manufactured by Merck), Trt Chloride resin (manufactured by Merck), and the like may be used.

Moreover, a linker may be disposed between such Amino-PEGA resin and an amino acid. Examples of such linker include 4-hydroxymethylphenoxyacetic acid (HMPA) and 4-(4-hydroxymethyl-3-methoxyphenoxy)-butylacetic acid (HMPB).

Examples of a fat-soluble protecting group include: carbonyl-containing groups such as a 9-fluorenylmethoxycarbonyl (Fmoc) group, a t-butyloxycarbonyl (Boc) group, and an allyloxycarbonyl (Alloc) group; protecting groups such as acyl groups such as an acetyl (Ac) group, an allyl group and a benzyl group. However, examples are not particularly limited thereto.

In order to introduce a fat-soluble protecting group into a desired peptide (or glycopeptide), when an Fmoc group is introduced for example, it can be introduced by adding 9-fluorenylmethyl-N-succinimidyl carbonate and sodium bicarbonate to the reaction system and then carrying out a reaction. The reaction may be carried out at a temperature between 0° C. and 50° C., and preferably at a room temperature, for approximately 1 to 5 hours.

As an amino acid protected by a fat-soluble protecting group, the aforementioned amino acids protected by the above described method may be used. In addition, commercially available products may also be used. Examples of such amino acid protected by a protecting group include Fmoc-Ser, Fmoc-Asn, Fmoc-Val, Fmoc-Leu, Fmoc-Ile, Fmoc-Ala, Fmoc-Tyr, Fmoc-Gly, Fmoc-Lys, Fmoc-Arg, Fmoc-His, Fmoc-Asp, Fmoc-Glu, Fmoc-Gln, Fmoc-Thr, Fmoc-Cys, Fmoc-Met, Fmoc-Phe, Fmoc-Trp, and Fmoc-Pro.

As esterification catalysts, known dehydrating condensing agents such as 1-mesitylenesulfonyl-3-nitro-1,2,4-triazole (MSNT), dicyclohexylcarbodiimide (DCC), and 1,3-diisopropylcarbodiimide (DIPCDI) may be used, for example. With regard to the usage ratio between an amino acid and a dehydrating condensing agent, 1 to 10 parts by weight of, and preferably 2 to 5 parts by weight of the dehydrating condensing agent is generally used with respect to 1 part by weight of the amino acid.

An esterification reaction is preferably carried out by placing a resin in a solid-phase column, washing the resin with a solvent, and then adding an amino acid solution thereto, for example. Examples of such washing solvent include dimethylformamide (DMF), 2-propanol, and methylene chloride. Examples of a solvent for dissolving amino acid include dimethyl sulfoxide (DMSO), DMF, and methylene chloride. Such esterification reaction may be carried out at a temperature between 0° C. and 50° C., and preferably at a room temperature, for approximately 10 minutes to 30 hours, and preferably for approximately 15 minutes to 24 hours.

During the reaction, it is also preferable that unreacted functional groups on the solid phase be acetylated using acetic anhydride or the like and be capped.

A fat-soluble protecting group may be dissociated by treating it with a base, for example. Examples of such base include piperidine and morpholine. The treatment is preferably carried out in the presence of a solvent. Examples of a solvent used herein include DMSO, DMF, and methanol.

The amidation reaction between a free amino group and a carboxyl group of any given amino acid whose amino group nitrogen is protected by a fat-soluble protecting group is preferably carried out in the presence of an activator and a solvent.

Examples of an activator include dicyclohexylcarbodiimide (DCC), 1-ethyl-3-(3-d imethylaminopropyl)carbodiimide hydrochloride (WSC/HCl), diphenylphosphoryl azide (DPPA), carbonyldiimidazole (CU), diethylcyanophosphonate (DEPC), 1,3-diisopropylcarbodiimide (DIPCI), benzotriazol-1-yloxy-tris(pyrrolidino)phosphonium hexafluorophosphate (PyBOP), 3-diethoxyphosphoryloxy-1,2,3-benzotriazin-4(3H)-one (DEPBT), 1-hydroxybenzotriazole (HOBt), hydroxysuccinimide (HOSu), dimethylaminopyridine (DMAP), 1-hydroxy-7-azabenzotriazole (HOAt), 3-hydroxy-4-oxo-3,4-dihydro-5-azabenzo-1,2,3-triazine (HODhbt), hydroxyphthalimide (HOPht), pentafluorophenol (Pfp-OH), 2-(1H-benzotriazol-1-yl)-1,1,3,3-tetramethyluronium hexafluorophosphate (HBTU), O-(7-azabenzotriazol-1-yl)-1,1,3,3-tetramethyluronium hexafluorophosphonate (HATU), and O-benzotriazol-1-yl-1,1,3,3-tetramethyluronium tetrafluoroborate (TBTU).

With regard to the amount of an activator used, 1 to 20 equivalent amounts of, preferably 1 to 10 equivalent amounts of, and more preferably 1 to 5 equivalent amounts of activator is used with respect to any given amino acid whose amino group nitrogen is protected by a fat-soluble protecting group.

The reaction proceeds only with the aforementioned activator. However, amine is preferably added as an auxiliary agent. As such amine, diisopropylethylamine (DIPEA), N-ethylmorpholine (NEM), N-methylmorpholine (NMM), N-methylimidazole (NMI), and the like can be used. With regard to the amount of such auxiliary agent used, 1 to 20 equivalent amounts of, preferably 1 to 10 equivalent amounts of, and more preferably 1 to 5 equivalent amounts of auxiliary agent is used with respect to any given amino acid whose amino group nitrogen is protected by a fat-soluble protecting group.

Examples of a solvent include DMSO, DMF, and methylene chloride. The reaction is carried out at a temperature between 0° C. and 50° C., and preferably at a room temperature, for approximately 10 to 30 hours, and preferably for approximately 15 minutes to 24 hours. During this reaction also, it is preferable that unreacted amino groups on the solid phase be acetylated using acetic anhydride or the like and be capped. The fat-soluble protecting group may be dissociated in the same manner as that described above.

In order to cleave a peptide chain from a resin, it is preferable to treat the resin with an acid. Examples of an acid used herein include trifluoroacetic acid (TFA) and hydrogen fluoride (HF). During the treatment, a highly reactive cation species can be generated from the fat-soluble protecting group used for amino acid and the linker on the resin. Thus, to capture such cation species, a nucleophilic reagent is preferably added. Examples of such nucleophilic reagent include triisopropylsilane (TIS), phenol, thioanisole, and ethanedithiol (EDT).

Thus, a peptide (or a glycopeptide) comprising an amino acid residue having an —SH group can be obtained.

Moreover, a method utilizing the reverse reaction of an enzyme including transglutaminase as a typical example may be applied to the thus obtained peptide or glycopeptide comprising an amino acid residue having an —SH group to add a sugar chain thereto, thereby obtaining a glycopeptide comprising an amino acid having an —SH group.

Furthermore, it is also possible to combine a sugar chain elongation reaction using transferase with the aforementioned method.

Among the peptides or glycopeptides as obtained above, a peptide (or a glycopeptide) comprising an amino acid residue having an —SH group at the N-terminus thereof can be ligated to a peptide (or a glycopeptide) having an α-carboxythioester portion at the C-terminus thereof according to a ligation method.

In the present specification, the term "ligation method" is used to include not only the native chemical ligation method (NCL method) described in Patent Document 1, but also include the application of such native chemical ligation method to peptides comprising non-natural amino acids or amino acid derivatives (for example, the threonine derivative A of Formula (1), a protected methionine, a sugar chain-added amino acid, etc.), as described in the after-mentioned examples. According to such ligation method, a peptide having a natural amide bond (peptide bond) at a ligation site can be produced.

According to the ligation method, ligation can be carried out on all cases of between a peptide and a peptide, between a peptide and a glycopeptide, and between a glycopeptide and a glycopeptide.

A peptide (or a glycopeptide) having an α-carboxythioester group at the C-terminus thereof, which is used in the ligation method, can be produced by a method known to persons skilled in the art, as described in Patent Document 1.

For example, as described in the after-mentioned examples, a solid-phase synthesis method is applied to obtain a protected peptide (or glycopeptide) whose amino groups on the amino acid side chain and at the N-terminus are protected. A carboxyl group on the C-terminal side thereof is condensed with benzylthiol, using PyBOP(Benzotriazole-1-yl-oxy-tris-pyrrolidino-phosphonium hexafluorophosphate)/DIPEA as a condensing agent in a liquid phase. Thereafter, the chain of the amino acid is deprotected using a 95% TFA solution to obtain a peptide (or a glycopeptide) having an α-carboxythioester group at the C-terminus thereof.

The ligation method can be carried out using a method known to persons skilled in the art, as described in Patent Document 1, or by referring to the descriptions of the after-mentioned examples. For example, a first peptide having an α-carboxythioester group represented by —C(=O)—SR at the C-terminus thereof and a second peptide comprising an amino acid residue having an —SH group at the N-terminus thereof are prepared, while referring to the aforementioned descriptions. In the first peptide, R is not particularly limited, as long as it does not interfere a thiol exchange reaction and it acts as a leaving group in a nucleophilic substitution reaction on a carbonyl carbon. Preferably, such R may be selected from among benzyl-type groups such as benzylmercaptan, aryl-type groups such as thiophenol or 4-(carboxymethyl)-thiophenol, alkyl-type groups such as 2-mercaptoethane-sulfonate or 3-mercaptopropionic acid amide, and the like. The —SH group at the N-terminus of the second peptide may be protected by a protecting group, as desired. This protecting group is removed at a desired time point before the subsequent ligation reaction, and the second peptide having an —SH group at the N-terminus thereof reacts with the first peptide. For example, if it is a protecting group that is spontaneously removed under conditions in which ligation takes place, the second peptide protected by the protecting group may be directly used in the subsequent ligation reaction.

The two peptides are mixed with each other in a solution such as a 100 mM phosphate buffer in the presence of catalytic thiol such as 4-mercaptophenylacetic acid, benzylmercaptan or thiophenol, as necessary. Preferably the reaction is carried out, using 0.5 to 2 equivalent amounts of the second peptide and approximately 5 equivalent amounts of the catalytic thiol with respect to 1 equivalent amount of the first peptide. The reaction is preferably carried out under conditions consisting of pH 6.5 to 7.5 and a temperature between 20° C. and 40° C. for approximately 1 to 30 hours. The progress of the reaction can be confirmed by a known method, in which HPLC, MS, and the like are combined.

To the reaction product, a reducing agent such as dithiothreitol (DTT) or tris(2-carboxyethyl)phosphine (TCEP) hydrochloride is added to suppress side reactions, and the reaction product is purified as desired, so that the first peptide can be ligated to the second peptide.

In a case in which peptides having different R groups exist among the peptides having a carboxythioester portion (—C=O—SR) at the C-terminus thereof, the order of ligation reactions can be altered (see Protein Science (2007), 16: 2056-2064, etc.). Thus, when ligation is carried out multiple times, the order of ligation reactions may be taken into consideration. For example, when an aryl group, a benzyl group, and an alkyl group exist as R, the ligation reaction generally progresses in this order.

In the present invention, a method for producing a peptide (or a glycopeptide) characterized in that an —SH group of a peptide (or a glycopeptide) comprising an amino acid residue having the —SH group is converted to an —OH group will be specifically described. As raw materials, the peptide or glycopeptide obtained by the aforementioned method is used. In one aspect of the present invention, a peptide or a glycopeptide obtained by a ligation method is preferably used. Subsequently, the following steps (a) to (c) are carried out:

(a) allowing an —SH group in a peptide to react with a methylating agent to convert the —SH group to an -SMe group;

(b) allowing the -SMe group obtained in the step (a) to react with a cyanizing agent to produce a reaction intermediate; and (c) converting the reaction intermediate obtained in the step (b) to a peptide comprising an amino acid residue having an —OH group under more basic conditions than the conditions in the step (b). Hereafter, the case of using a peptide as a raw material will be exemplified.

Step (a)

The methylating agent used in the methylation of the step (a) is not particularly limited, as long as it is capable of converting the —SH group in the peptide to the -SMe group. Examples of such methylating agent include iodomethane and methyl-4-nitrobenzenesulfonate.

With regard to the amount of a methylating agent used, 1 to 1,000 equivalent amounts of, preferably 10 to 100 equivalent amounts of, and more preferably 15 to 30 equivalent amounts of the methylating agent can be used with respect to a single residue of the —SH group of the raw material peptide. The methylation reaction is desirably carried out at a temperature between 0° C. and 50° C., and preferably between 20° C. and 30° C., for approximately 10 minutes to 30 hours, and preferably for approximately 15 minutes to 1 hour.

A buffer solution is preferably used as a solvent in the methylation reaction. A buffer solution having pH 7 to 9, and particularly pH 8 to 9, can be preferably used. For example, a 0.25 M Tris-HCl buffer solution (6 M guanidine hydrochloride solution, containing 3.3 mM EDTA, pH 8.6) or the like can be used.

In a case in which a cysteine residue is contained as an amino acid in a peptide and in which the cysteine residue is not intended to be converted to a serine residue and it is allowed to exist as a cysteine residue in a peptide obtained by the production method of the present invention, such cysteine is protected and it is introduced in the form of a protected cysteine into a peptide according to a known method. Thereby, the —SH group of the cysteine can be prevented from being methylated in the step (a). Taking into consideration a thiol exchange reaction, a treatment with acid, a treatment with base, etc. performed in each step of the production method of the present invention, an appropriate protecting group can be used as a protecting group for cysteine. Examples of such protecting group include an acetamidem-ethyl (Acm) group, a benzyl group, an acetamide group, and a trityl group. Preferably, an Acm group can be used. After the steps (a) to (c), the protected cysteine residue is deprotected using a known method. For example, when a protected cysteine that has been protected by a protecting group such as an Acm group, a nitrobenzyl group, or a trityl group, is introduced, such protected cysteine is converted to a cysteine residue by adding a step of applying a deprotection method using a silver acetate aqueous solution, a deprotection method using light, a deprotection method involving a treatment with acid, or other methods. Thus, a cysteine residue is allowed to exist in the peptide obtained by the production method of the present invention.

In one aspect of the present invention, it is also possible to obtain a peptide having an —OH group by converting an -SMe group of a peptide having the SMe group to —OH group. In such a case, the aforementioned step (a) can be omitted.

Step (b)

From the viewpoint of safety and the like, cyanogen bromide, phenylcyanate, or the like can be used as a cyanizing agent in the step (b), for example. Preferably, cyanogen bromide, which can be easily procured, can be used.

With regard to the amount of a cyanizing agent used, 1 to 1,000 equivalent amounts of, preferably 10 to 100 equivalent amounts of, and more preferably 15 to 30 equivalent amounts of the cyanizing agent can be used with respect to a single -SMe group. The reaction with the cyanizing agent is desirably carried out at a temperature between 0° C. and 50° C., and preferably between 30° C. and 40° C., for approximately 30 minutes to 100 hours, and preferably for approximately 12 hours to 50 hours.

The reaction with the cyanizing agent is carried out under acidic conditions, and it is particularly preferably carried out at pH 2 to 3. Using an acidic water-soluble substance, and specifically using formic acid, trifluoroacetic acid, methanesulfonic acid, or the like, the reaction can be carried out under acidic conditions. During the reaction, in order to prevent the oxidation of sulfur atoms, it is particularly preferable that the used acidic water-soluble substance have been deaerated. In addition, from the viewpoint of the stability of the cyanizing agent, the reaction is preferably carried out under shading conditions.

As a solvent, the aforementioned water-soluble solvent having pH 2 to 3, such as a 80% formic acid solution, a 70% formic acid solution, or a 2% trifluoroacetic acid/39% acetonitrile-containing aqueous solution, can be preferably used.

An example of the reaction intermediate obtained in the step (b) is an ester form having the following structure:

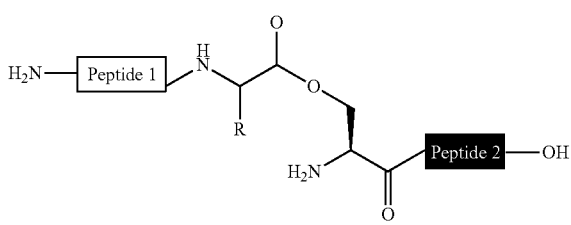

When a methionine residue is contained as an amino acid in the peptide, it is preferable to distinguish the -SMe group contained in the methionine residue from the -SMe group obtained in the step (a). In the present specification, the protected methionine is not particularly limited, as long as it is a compound that does not react with the cyanizing agent in the step (b). An example of such protected methionine is a sulfoxide-type methionine (Met(O): —CH$_2$—CH$_2$—S(=O)—CH$_3$). As described in the after-mentioned Example 5, a protected methionine (for example, Met(O)) is introduced into the peptide using a known method, so that a methionine residue can be distinguished from the -SMe group obtained in the step (a), and the methionine residue becomes inactive on the reaction with the cyanizing agent in the step (b). Thereafter, the protected methionine residue is converted to a methionine residue using a known method, as appropriate (the after-mentioned step (e)). Thus, a peptide having a methionine residue can also be obtained by the production method of the present invention.

Moreover, an oxidized cysteine, which is a by-product formed during the reaction with the cyanizing agent in the step (b), can be removed, as necessary. In such removing step, a mixture comprising the reaction intermediate obtained in the step (b) may be reacted at a room temperature for approximately 30 minutes in the presence of ammonium iodide and dimethyl sulfide, for example, and thereafter, the reaction solution may be separated and washed. Such removing step may be carried out at any time point after the step (b), and it may be preferably carried out after the step (c).

Step (c)

In the step (c), under more basic conditions than those in the step (b), a peptide comprising an amino acid residue having an —OH group is obtained by an intramolecular acyl rearrangement from O— to N— of the reaction intermediate obtained in the step (b).

The basic conditions in the step (c) may be either acidic or neutral, as long as they are more basic conditions than the conditions in the step (b). More specifically, the basic conditions in the step (c) are not particularly limited, as long as they are conditions in which an —NH$_2$ group on a C atom adjacent to the ester bond of the reaction intermediate obtained in the step (b) is not protonated. From the viewpoint of efficient conversion of the reaction intermediate to a peptide having an —OH group, weakly basic conditions or strongly basic conditions can be applied.

When the basic conditions in the step (c) are weakly basic conditions, the pH is pH 7 to 9, and preferably pH 7 to 8. For example, by adding to a solution, a basic compound that is used as a pH adjuster known to persons skilled in the art, such as guanidine, disodium phosphate, Tris, or sodium bicarbonate, weakly basic conditions can be prepared. During this operation, with regard to the amount of a basic compound used, 1 to 1,000 equivalent amounts of, preferably 10 to 100 equivalent amounts of, and more preferably 15 to 30 equivalent amounts of such basic compound may be used with respect to a raw material peptide.

When the basic conditions in the step (c) are weakly basic conditions, the reaction is desirably carried out at a temperature between 0° C. and 50° C., and preferably between 20° C. and 40° C., for approximately 10 minutes to 30 hours, and preferably for approximately 15 minutes to 30 hours. The reaction is desirably carried out in a buffer solution having pH 7 to 9, and preferably pH 7 to 8. For example, the step (c) may be carried out in a 0.2 M phosphate buffer (containing a 6 M guanidine hydrochloride solution, pH 7.2).

When the basic conditions in the step (c) are weakly basic conditions, the pH may be further decreased, and the step (c) may be terminated. Otherwise, the routine may proceed to a purification step using HPLC or the like, without changing the pH.

When the basic conditions in the step (c) are strongly basic conditions, the pH is pH 9 to 13, and preferably pH 10 to 11. Such strongly basic conditions are preferably conditions in which a compound that has excessively reacted with a hydroxyl group can be removed by hydrolysis. By adding to a solution, a basic water-soluble substance such as a hydrazine hydrate, a 50 mM sodium hydroxide aqueous solution, or the like, strongly basic conditions can be prepared. During this operation, with regard to the amount of a basic water-soluble substance used, 0.5 to 100 equivalent amounts of, preferably 0.1 to 10 equivalent amounts of, and more preferably 0.5 to 1 equivalent amounts of such basic water-soluble substance may be used with respect to a raw material peptide. For example, the step (c) may be carried out in a 5% hydrazine aqueous solution having pH 10 to 11.

When the basic conditions in the step (c) are strongly basic conditions, a peptide comprising an amino acid residue having an —OH group can be obtained by an intramolecular acyl rearrangement from O— to N— of the reaction intermediate obtained in the step (b), and at the same time, decyanization (a decyanization reaction for removing excessively reacted cyanizing agents by hydrolysis), deformylation (a deformylation reaction of excessively reacted formic acids), and the like may occur on the excessively reacted —OH groups in the steps (a) and (b).

When the basic conditions in the step (c) are strongly basic conditions, the step (c) is desirably carried out at a temperature between 0° C. and 50° C., and preferably between 20° C. and 30° C., for approximately 5 minutes to 3 hours, preferably for approximately 5 minutes to 1 hour, and more preferably for approximately 5 minutes to 10 minutes. When the basic conditions in the step (c) are strongly basic conditions, if the step (c) is carried out for a long period of time, side reactions such as racemization and the cleavage of a peptide bond may occur.

When the basic conditions in the step (c) are strongly basic conditions, the step (c) may be terminated by decreasing the pH to pH 4 to 9, and preferably to pH 5 to 9, for example, around pH 7, or pH 8 to 9.

In the step (c), it is assumed that the configuration of the position 13 of the obtained amino acid residue having an —OH group is inverted from that of the reaction intermediate obtained in the step (b).

Step (d)

When a peptide containing a protected methionine residue is used as a raw material, the following step (d) is further carried out after the step (b) or (c), as desired: (d) deprotecting the protected methionine.

Deprotection may be carried out using a method known to persons skilled in the art, depending on the type of the protected methionine used. When a sulfoxide-type methionine (Met(O)) is introduced as a protected methionine, for example, such protected methionine is converted to methionine by adding a reduction step using an ammonium iodide/dimethyl sulfide/TFA mixed solution or the like. From the viewpoint of the prevention of the occurrence of side reactions, the step (d) is preferably carried out after the step (c).

Thus, in the case of obtaining a peptide having a methionine residue as well, the production method of the present invention can be applied.

For the purification of the obtained product, a method for obtaining a 97% or more purified product under several types of high performance liquid chromatography conditions is preferably applied. Specific examples of such method include crystallization, a transactional partition method, partition chromatography, a gel filtration method, ion exchange chromatography, and high performance liquid chromatography. Preferably, high performance liquid chromatography or the like can be applied.

In addition to the aforementioned steps, a step of adding a sugar chain may be further carried out. Such addition of a sugar chain can be carried out on both a peptide and a glycopeptide. Such addition of a sugar chain can be carried out at any time point, as long as a glycopeptide of interest can be obtained. It is preferably carried out after the step (c).

The addition of a sugar chain can be carried out by a method utilizing the reverse reaction of an enzyme including transglutaminase as a typical example, or by a method performed by referring to the descriptions of International Publication WO2005/010053, as described below.

First, a haloacetamide complex-type sugar chain derivative is produced by allowing it to react with a peptide as obtained above (in particular, a peptide comprising: an amino acid having two or more carboxyl groups in its molecule, such as aspartic acid or glutamic acid; an amino acid having two or more amino groups in its molecule, such as lysine, arginine, histidine, or tryptophan; an amino acid having a hydroxyl group in its molecule, such as serine, threonine, or tyrosine; an amino acid having a thiol group in its molecule, such as cysteine; or an amino acid having an amide group in its molecule, such as asparagine or glutamine, and among them, particularly, a peptide comprising aspartic acid, glutamic acid, lysine, arginine, serine, threonine, cysteine, asparagine, or glutamine). The aforementioned reaction may be carried out at a temperature generally between 0° C. and 80° C., preferably between 10° C. and 60° C., and more preferably between 15° C. and 35° C. Preferably, the reaction time is generally approximately 30 minutes to 5 hours. After completion of the reaction, a reaction product may be purified by a known method (for example, high performance liquid chromatography (HPLC)), as appropriate.

The haloacetamide complex-type sugar chain derivative is a compound formed by substituting a hydroxyl group binding to the carbon at position 1 of a complex-type asparagine-bound sugar chain with —NH—(CO)—$(CH_2)_a$—$CH_2X$ (wherein X represents a halogen atom, and a represents an integer that is not particularly limited unless it interferes a linker function of interest, and preferably represents an integer from 0 to 4), for example.

Specifically, the haloacetamide complex-type sugar chain derivative is allowed to react with the above obtained peptide in a phosphate buffer at a room temperature. After completion of the reaction, the reaction solution is purified by HPLC to obtain a sugar chain-added glycopeptide.

It is also possible to combine a sugar chain elongation reaction using transferase with the aforementioned method. The thus obtained glycopeptide is also included in the scope of the present invention.

EXAMPLES

Hereinafter, the present invention will be specifically described in the following examples. However, these examples are not intended to limit the scope of the present invention.

Example 1

Production of Ac-Ala-Ser-Gly-Leu

Wang resin (manufactured by Merck) (100 μmol) was placed in a solid-phase synthesis column, and it was then fully washed with methylene chloride (DCM) and DMF. Thereafter, the resultant was fully swollen with DCM. Fmoc-Leu (0.50 mmol), MSNT (0.50 mmol), and N-methylimidazole (0.375 mmol) were dissolved in DCM (2 mL), and the obtained solution was then placed in the solid-phase synthesis column, followed by stirring at 25° C. for 1 hour. It is to be noted that the volume of the DCM can also be set at 1.5 mL. After completion of the stirring operation, the resin was fully washed with DCM and DMF, and the Fmoc group was treated with a 20% piperidine/DMF solution (2 mL) for 15 minutes for deprotection. It is to be noted that the present deprotection treatment can also be carried out for 10 minutes. After washing with DMF, as for the subsequent elongation of a peptide chain, amino acids were successively condensed according to the below-mentioned method.

An amino acid whose amino group had been protected by an Fmoc group, HOBt (67.6 mg, 0.50 mmol), and DIPCI (77.0 µL, 63.1 mg, 0.50 mmol) were dissolved in DMF (1 mL), and the obtained solution was then activated for 15 minutes. Thereafter, the solution was placed in the solid-phase synthesis column. It is to be noted that the volume of the DMF can also be set at 2 mL. After stirring at 25° C. for 1 hour, the Fmoc group was treated with a 20% piperidine/DMF solution (2 mL) for 20 minutes for deprotection. It is to be noted that the present deprotection treatment can also be carried out for 10 minutes. These operations were repeated, so that amino acids were successively condensed. As amino acids protected by the Fmoc groups, Fmoc-Gly (148.7 mg, 0.50 mmol), Fmoc-Cys(Trt) (292.9 mg, 0.50 mmol), and Fmoc-Ala (155.7 mg, 0.50 mmol) were used, and a 4-residue peptide having a protecting group, Fmoc-Ala-Cys(Trt)-Gly-Leu (SEQ ID NO: 1), was obtained on the solid-phase resin. Thereafter, the Fmoc group was treated with a 20% piperidine/DMF solution (2 mL) on the resin for 20 minutes for deprotection, and free amino groups were then protected by acetyl using a 20% acetic anhydride/DMF solution (2 mL). It is to be noted that the volume of the 20% acetic anhydride/DMF solution can also be set at 1.7 mL. After washing with DMF and DCM, a previously prepared reagent (TFA/water/phenol/thioanisole/EDT (1,2-ethanedithiol)/TIPS=81.5/5/5/5/2.5/1) was added to such an extent that the resin was sufficiently immersed therein, and it was then stirred at 25° C. for 2 hours. The resin was removed by filtration, and the reaction solution was then concentrated under a reduced pressure. The obtained residue was purified by HPLC (Vydac column C8, 250×10 mm; developing solvents A: 0.1% TFA aqueous solution; and B: 0.08% TFA; acetonitrile:water=90:10; gradients A:B=85:15→50:50; 60 minutes; flow rate: 3.0 ml/min) to obtain a 4-residue peptide having a protecting group, Ac-Ala-Cys-Gly-Leu (SEQ ID NO: 2).

30 mg (73 µmol) of the obtained 4-residue peptide (SEQ ID NO: 2) was placed in a round-bottom flask, and it was dissolved in 73 mL of a 0.25 M Tris-HCl buffer (pH 8.6; containing 6 M guanidine hydrochloride solution and 3.3 mM EDTA) and 24 mL of acetonitrile. Thereafter, methyl-4-nitrobenzenesulfonate (316 mg) was added to the solution at 25° C. Thirty minutes later, a 10% TFA solution (7.3 mL) was added thereto, so that the pH of the solution was adjusted to be pH 4. Thereafter, diethyl ether was added thereto to carry out an extraction operation. After completion of the concentration, the obtained residue was placed in an ODS column to carry out purification, thereby obtaining 25 mg of a 4-residue peptide having a protecting group, Ac-Ala-Cys(Me)-Gly-Leu (SEQ ID NO: 3), wherein the sulfur atom of the cysteine residue was methylated.

ESI-MS: Calcd for $C_{17}H_{30}N_4O_6S$: $[M+1H]^{1+}$ 419.2. Found, 419.1

6.5 mg (15 µmol) of the obtained 4-residue peptide (SEQ ID NO: 3) wherein the sulfur atom of the cysteine residue had been methylated was placed in an Eppendorf tube, and it was dissolved in an 80% formic acid solution (6.5 mL). Thereafter, 159.0 mg (1.5 mmol) of cyanogen bromide was added to the solution at 25° C. The reactor was shaded from light, and a reaction was then carried out at 37° C. 28.5 hours later, the reaction solution was frozen to terminate the reaction. The residue obtained after the freeze-drying of the reaction solution was purified by HPLC (Vydac column C4, 250×4.6 mm; developing solvents A: 0.1% TFA aqueous solution; and B: 0.08% TFA; acetonitrile:water=90:10; gradients A:B=100:0→60:40; 30 minutes; flow rate: 1.0 ml/min) to obtain 3.8 mg of an ester form as a reaction intermediate.

ESI-MS: Calcd for $C_{16}H_{28}N_4O_7$: $[M+1H]^{1+}$ 389.4. Found, 389.2

5 mg of the obtained reaction intermediate was placed in an Eppendorf tube in the same above manner, and it was dissolved in 0.6 mL of a phosphate buffer (pH 7.2; containing 6 M guanidine hydrochloride), followed by a reaction at 37° C. One hour later, after confirming by HPLC that the reaction had been terminated, the reaction solution was purified by HPLC (Vydac column C4, 250×4.6 mm; developing solvents A: 0.1% TFA aqueous solution; and B: 0.08% TFA; acetonitrile:water=90:10; gradients A:B=100:0→60:40; 30 minutes; flow rate: 1.0 ml/min) to obtain 3.5 mg of a 4-residue peptide of interest having a protecting group, Ac-Ala-Ser-Gly-Leu (SEQ ID NO: 4). It is to be noted that the reaction time can also be set at 30 minutes.

ESI-MS: Calcd for $C_{16}H_{28}N_4O_7$: $[M+1H]^{1+}$ 389.4. Found, 389.1

Example 2

Production of Val-Asp-Lys-Ala-Val-Ser-Gly-Leu

Wang resin (manufactured by Merck) (100 µmol) was placed in a solid-phase synthesis column, and it was then fully washed with methylene chloride (DCM) and DMF. Thereafter, the resultant was fully swollen with DCM. Fmoc-Leu (0.50 mmol), MSNT (0.50 mmol), and N-methylimidazole (0.375 mmol) were dissolved in DCM (2 mL), and the obtained solution was then placed in the solid-phase synthesis column, followed by stirring at 25° C. for 1 hour. It is to be noted that the volume of the DCM can also be set at 1.5 mL. After completion of the stirring operation, the resin was fully washed with DCM and DMF, and the Fmoc group was treated with a 20% piperidine/DMF solution (2 mL) for 15 minutes for deprotection. It is to be noted that the present deprotection treatment can also be carried out for 10 minutes. After washing with DMF, as for the subsequent elongation of a peptide chain, amino acids were successively condensed according to the below-mentioned method.

An amino acid whose amino group had been protected by an Fmoc group, HOBt (67.6 mg, 0.50 mmol), and DIPCI (77.0 µL, 63.1 mg, 0.50 mmol) were dissolved in DMF (1 mL), and the obtained solution was then activated for 15 minutes. Thereafter, the solution was placed in the solid-phase synthesis column. It is to be noted that the volume of the DMF can also be set at 2 mL. After stirring at 25° C. for 1 hour, the Fmoc group was treated with a 20% piperidine/DMF solution (2 mL) for 20 minutes for deprotection. It is to be noted that the present deprotection treatment can also be carried out for 10 minutes. These operations were repeated, so that amino acids were successively condensed. As amino acids protected by the Fmoc groups, Fmoc-Gly (148.7 mg, 0.50 mmol), Fmoc-Cys (Trt) (292.9 mg, 0.50 mmol), Fmoc-Val (169.7 mg, 0.50 mmol), Fmoc-Ala (155.7 mg, 0.50 mmol), Fmoc-Lys (Boc) (234.3 mg, 0.50 mmol), Fmoc-Asp (OtBu) (205.8 mg, 0.50 mmol), and Fmoc-Val (169.7 mg, 0.50 mmol) were used, and a 8-residue peptide having a protecting group, Fmoc-Val-Asp(OtBu)-Lys(Boc)-Ala-Val-Cys(Trt)-Gly-Leu (SEQ ID NO: 5), was obtained on the solid-phase resin. Thereafter, the Fmoc group was treated with a 20% piperidine/DMF solution (2 mL) on the resin for 20 minutes for deprotection, and the reaction solution was then washed with DMF and DCM. Thereafter, a previously prepared reagent K (TFA/water/phenol/thioanisole/EDT=82.5/5/5/5/2.5) was added to such an extent that the resin was sufficiently immersed therein, and it was then stirred at 25° C. for 2 hours. It is to be noted that, instead of the reagent K, TFA/water/phenol/thioanisole/EDT/TIPS=81.5/5/5/5/2.5/1.0 may also be used. The resin was removed by filtration, and the reaction solution was then concentrated under a reduced pressure. The obtained residue was purified by HPLC (Vydac column C18, 250×10 mm; developing solvents A: 0.1% TFA aqueous solution; and B: 0.08% TFA; acetonitrile:water=90:10; gradients A:B=85:15→50:50; 15 minutes; flow rate: 2.5 ml/min) to obtain an 8-residue peptide, Val-Asp-Lys-Ala-Val-Cys-Gly-Leu (SEQ ID NO: 6).

32 mg (40 μmol) of the obtained 8-residue peptide (SEQ ID NO: 6) was placed in a round-bottom flask, and it was dissolved in 40 mL of a 0.25 M Tris-HCl buffer (pH 8.6; containing 6 M guanidine hydrochloride solution and 3.3 mM EDTA) and 13 mL of acetonitrile. Thereafter, methyl-4-nitrobenzenesulfonate (261 mg) was added to the solution at 25° C. One hour later, a 10% TFA solution (3.8 mL) was added thereto, so that the pH of the solution was adjusted to be pH 4. Thereafter, diethyl ether was added thereto to carry out an extraction operation. After completion of the concentration, the obtained residue was placed in an ODS column to carry out purification, thereby obtaining 30 mg of a 8-residue peptide, Val-Asp-Lys-Ala-Val-Cys(Me)-Gly-Leu (SEQ ID NO: 7), wherein the sulfur atom of the cysteine residue was methylated.

ESI-MS: Calcd for $C_{35}H_{64}N_9O_{11}S$: $[M+1H]^{1+}$ 819.0. Found, 818.8

29 mg (36 μmol) of the obtained 8-residue peptide (SEQ ID NO: 7) wherein the sulfur atom of the cysteine residue had been methylated was placed in a round-bottom flask, and it was dissolved in 15 mL of an 80% formic acid solution. Thereafter, 381 mg (3.6 mmol) of cyanogen bromide was added to the solution at 25° C. The reactor was shaded from light, and a reaction was then carried out at 25° C. Thirty-two hours later, the reaction solution was frozen to terminate the reaction. The residue obtained after the freeze-drying of the reaction solution was purified by HPLC (Vydac column C8, 250×10 mm; developing solvents A: 0.1% TFA aqueous solution; and B: 0.08% TFA; acetonitrile:water=90:10; gradients A:B=90:10→70:30; 60 minutes; flow rate: 4.0 ml/min) to obtain 18 mg of an ester form as a reaction intermediate.

ESI-MS: Calcd for $C_{34}H_{62}N_9O_{12}$: $[M+1H]^{1+}$ 788.9. Found, 788.5

5 mg of the obtained reaction intermediate was placed in an Eppendorf tube, and it was dissolved in 0.63 mL of a phosphate buffer (pH 7.2; containing 6 M guanidine hydrochloride), followed by a reaction at 37° C. 9.25 hours later, after confirming that the reaction had been terminated, the reaction solution was purified by HPLC (Vydac column C4, 250×4.6 mm; developing solvents A: 0.1% TFA aqueous solution; and B: 0.08% TFA; acetonitrile:water=90:10; gradients A:B=100:0→40:60; 30 minutes; flow rate: 1.0 ml/min) to obtain 4.1 mg of a 8-residue peptide of interest, Val-Asp-Lys-Ala-Val-Ser-Gly-Leu (SEQ ID NO: 8). It is to be noted that the reaction time can also be set at 7.25 hours.

ESI-MS: Calcd for $C_{34}H_{62}N_9O_{12}$: $[M+1H]^{1+}$ 788.9. Found, 788.7

Example 3

Production of
Leu-Phe-Arg-Val-Tyr-Ser-Asn-Phe-Leu-Arg-Gly

Wang resin (manufactured by Merck) (100 μmol) was placed in a solid-phase synthesis column, and it was then fully washed with methylene chloride (DCM) and DMF. Thereafter, the resultant was fully swollen with DCM. Fmoc-Gly (0.50 mmol), MSNT (0.50 mmol), and N-methylimidazole (0.375 mmol) were dissolved in DCM (2 mL), and the obtained solution was then placed in the solid-phase synthesis column, followed by stirring at 25° C. for 1 hour. It is to be noted that the volume of the DCM can also be set at 1.5 mL. After completion of the stirring operation, the resin was fully washed with DCM and DMF, and the Fmoc group was treated with a 20% piperidine/DMF solution (2 mL) for 15 minutes for deprotection. It is to be noted that the present deprotection treatment can also be carried out for 10 minutes. After washing with DMF, as for the subsequent elongation of a peptide chain, amino acids were successively condensed according to the below-mentioned method.

An amino acid whose amino group had been protected by an Fmoc group, HOBt (67.6 mg, 0.50 mmol), and DIPCI (77.0 μL, 63.1 mg, 0.50 mmol) were dissolved in DMF (1 mL), and the obtained solution was then activated for 15 minutes. Thereafter, the solution was placed in the solid-phase synthesis column. After stirring at 25° C. for 1 hour, the Fmoc group was treated with a 20% piperidine/DMF solution (2 mL) for 20 minutes for deprotection. It is to be noted that the present deprotection treatment can also be carried out for 10 minutes. These operations were repeated, so that amino acids were successively condensed. As amino acids protected by the Fmoc groups, Fmoc-Arg (Pbf) (324.4 mg, 0.50 mmol), Fmoc-Leu (176.7 mg, 0.50 mmol), Fmoc-Phe (193.7 mg, 0.50 mmol), Fmoc-Asn (177.2 mg, 0.50 mmol), Fmoc-Cys (Trt) (292.9 mg, 0.50 mmol), Fmoc-Tyr (tBu) (229.8 mg, 0.50 mmol), Fmoc-Val (169.7 mg, 0.50 mmol), Fmoc-Arg (Pbf) (324.4 mg, 0.50 mmol), Fmoc-Phe (193.7 mg, 0.50 mmol), and Fmoc-Leu (176.7 mg, 0.50 mmol) were used, and a 11-residue peptide having a protecting group, Fmoc-Leu-Phe-Arg(Pbf)-Val-Tyr(tBu)-Cys(Trt)-Asn-Phe-Leu-Arg (Pbf)-Gly (SEQ ID NO: 9), was obtained on the solid-phase resin. Thereafter, the Fmoc group was treated with 2 mL of a 20% piperidine/DMF solution on the resin for 20 minutes for deprotection. It is to be noted that the present deprotection treatment can also be carried out for 10 minutes. The reaction solution was washed with DMF and DCM. Thereafter, a previously prepared reagent K (TFA/water/phenol/thioanisole/EDT=82.5/5/5/5/2.5) was added to such an extent that the resin was sufficiently immersed therein, and it was then stirred at 25° C. for 2 hours. It is to be noted that, instead of the reagent K, TFA/water/phenol/thioanisole/EDT/TIPS=81.5/5/5/5/2.5/1.0 may also be used. The resin was removed by filtration, and the reaction solution was then concentrated under a reduced pressure. The obtained residue was purified by HPLC (Vydac column C18, 250×10 mm; developing solvents A: 0.1% TFA aqueous solution; and B: 0.08% TFA; acetonitrile:water=90:10; gradients A:B=70:30→40:60; 15 minutes; flow rate: 2.0 ml/min) to obtain a 11-residue peptide, Leu-Phe-Arg-Val-Tyr-Cys-Asn-Phe-Leu-Arg-Gly (SEQ ID NO: 10).

21 mg (15 μmol) of the obtained 11-residue peptide (SEQ ID NO: 10) was placed in a round-bottom flask, and it was dissolved in 15 mL of a 0.25 M Tris-HCl buffer (pH 8.6; containing 6 M guanidine hydrochloride solution and 3.3 mM EDTA) and acetonitrile (5 mL). Thereafter, methyl-4-nitrobenzenesulfonate (66 mg) was added to the solution at 25° C. Thirty minutes later, a 10% TFA solution (1.5 mL) was added thereto, so that the pH of the solution was adjusted to be pH 4. Thereafter, diethyl ether was added thereto to carry out an extraction operation. After completion of the concentration, the obtained residue was placed in an ODS column to carry out purification, thereby obtaining 19 mg of a 11-residue peptide, Leu-Phe-Arg-Val-Tyr-Cys(Me)-Asn-Phe-Leu-Arg-Gly (SEQ ID NO: 11), wherein the sulfur atom of the cysteine residue was methylated.

ESI-MS: Calcd for $C_{66}H_{100}N_{18}O_{14}S$: $[M+2H]^{2+}$ 701.4. Found, 701.5

18 mg (13 μmol) of the obtained 11-residue peptide (SEQ ID NO: 11) wherein the sulfur atom of the cysteine residue had been methylated was placed in a round-bottom flask, and it was dissolved in 5.4 mL of a 2.4 mM 80% formic acid solution. Thereafter, 136 mg (1.3 mmol) of cyanogen bromide was added to the solution at 25° C. The reactor was shaded from light, and a reaction was then carried out at 25° C. Approximately fifty hours later, the reaction solution was frozen to terminate the reaction. The residue obtained after the freeze-drying of the reaction solution was purified by HPLC (Vydac column C8, 250×10 mm; developing solvents A: 0.1% TFA aqueous solution; and B: 0.08% TFA; acetonitrile:water=90:10; gradients A:B=85:15→50:50; 60 minutes; flow rate: 3.0 ml/min) to obtain 7.5 mg of an ester form as a reaction intermediate.

ESI-MS: Calcd for $C_{65}H_{100}N_{18}O_{15}$: $[M+2H]^{2+}$ 686.4. Found, 686.5

7 mg of the obtained reaction intermediate was placed in an Eppendorf tube, and it was dissolved in 0.50 mL of a phosphate buffer (pH 7.2; containing 6 M guanidine hydrochloride), followed by a reaction at 37° C. One hour later, after confirming that the reaction had been terminated, the reaction solution was purified by HPLC (Vydac column C4, 250×4.6 mm; developing solvents A: 0.1% TFA aqueous solution; and B: 0.08% TFA; acetonitrile:water=90:10; gradients A:B=80:20→40:60; 30 minutes; flow rate: 1.0 ml/min) to obtain 5.4 mg of a 11-residue peptide of interest, Leu-Phe-Arg-Val-Tyr-Ser-Asn-Phe-Leu-Arg-Gly (SEQ ID NO: 12).

ESI-MS: Calcd for $C_{65}H_{100}N_{18}O_{15}$: $[M+2H]^{2+}$ 686.4. Found, 686.4

Example 4

Production of Ala-Leu-Leu-Val-Asn(Oligosaccharide chain)-Ser-Ser-Gln-Pro-Trp-Glu-Pro-Leu-Gln-Leu-His-Val-Asp-Lys-Ala Amino-PEGA resin (manufactured by Merck) (100 μmol) was placed in a solid-phase synthesis column, and it was then fully washed with methylene chloride (DCM) and DMF. Thereafter, the resultant was fully swollen with DCM. 4-hydroxymethyl-3-methoxyphenoxy butyric acid (HMPB) (0.25 mmol), TBTU (0.25 mmol), and N-ethylmorpholine (0.25 mmol) were dissolved in DMF (2 mL), and the obtained solution was then placed in the column, followed by stirring at 25° C. for 4 hours. Thereafter, the resin was fully washed with DMF and DCM to obtain an HMPB-PEGA resin. The obtained HMPB-PEGA resin was used as a solid-phase carrier in solid-phase synthesis.

Fmoc-Ser (tBu) (0.50 mmol), MSNT (0.50 mmol), and N-methylimidazole (0.375 mmol) were dissolved in DCM (2 ml), and the obtained solution was then placed in the solid-phase synthesis column, followed by a reaction at 25° C. for 3 hours. It is to be noted that the volume of the DCM can also be set at 2.5 mL. After completion of the stirring operation, the resin was washed with DCM and DMF, and the Fmoc group was treated with a 20% piperidine/DMF solution (2 mL) for 15 minutes for deprotection. It is to be noted that the present deprotection treatment can also be carried out for 10 minutes.

After washing with DMF, a resin corresponding to 2 μmol of 1-residue peptide was transferred into an Eppendorf tube. The sugar chain asparagine (10 mg, 3.6 μmol) represented by Formula (9) below and DEPBT (2 mg, 6 μmol) were dissolved in DMF (0.12 mL), and the obtained solution was then placed in an Eppendorf tube. DIPEA (0.68 μl, 4 μmol) was added thereto, and the obtained mixture was then stirred at 25° C. for 18 hours.

(9)

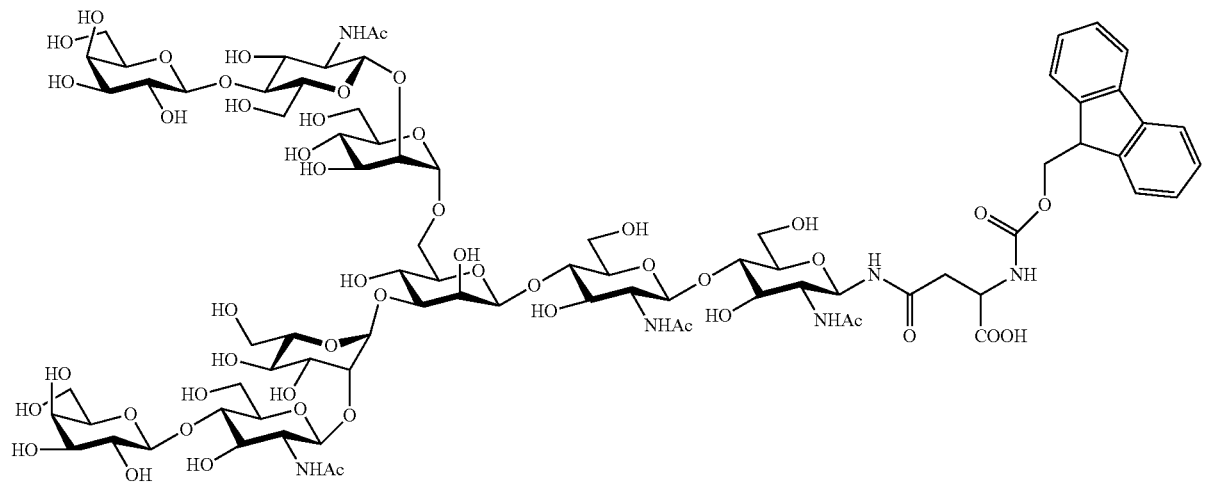

After completion of the stirring operation, the resin was washed with DCM and DMF. The Fmoc group was treated with a 20% piperidine/DMF solution (1 mL) for 15 minutes for deprotection. After washing with DMF, as for the subsequent elongation of a glycopeptide chain, amino acids were successively condensed according to the below-mentioned method.

An amino acid whose amino group had been protected by an Fmoc group, HOBt (1.35 mg, 0.01 mmol), and DIPCI (1.53 μL, 1.26 mg, 0.01 mmol) were dissolved in DMF (0.02 mL), and the obtained solution was then activated for 15 minutes. Thereafter, the solution was placed in the solid-phase synthesis column. After stirring at 25° C. for 1 hour, the Fmoc group was treated with a 20% piperidine/DMF solution (1 mL) for 20 minutes for deprotection. These operations were repeated, so that amino acids were successively condensed. As amino acids whose amino groups had been protected by the Fmoc groups, Fmoc-Val (3.4 mg, 0.01 mmol), Fmoc-Leu (3.5 mg, 0.01 mmol), Fmoc-Leu (3.5 mg, 0.01 mmol), and Fmoc-Ala (3.1 mg, 0.01 mmol) were used, and a 6-residue sugar-added peptide having a protecting group, Fmoc-Ala-Leu-Leu-Val-Asn(Oligosaccharide chain)-Ser (tBu) (SEQ ID NO: 13), was obtained on the solid-phase resin. Acetic acid:trifluoroethanol (=1:1) was added to this sugar-added peptide to such an extent that the resin was sufficiently immersed therein. Four hours later, the resin was removed by filtration, and a filtrate portion was then added to diethyl ether, which had been prepared separately to carry out crystallization. Thereafter, the solution portion was removed using a membrane filter, thereby obtaining a residue containing a 6-residue sugar chain-added peptide having a protecting group (SEQ ID NO: 13).

2 mg (0.55 µmol) of the obtained 6-residue sugar chain-added peptide having a protecting group (SEQ ID NO: 13), molecular sieve (MS) 4A (10 mg), and benzylmercaptan (2 µl, 16.4 µmol) were stirred in a DMF solvent (85 µl) in an argon atmosphere at −20° C. for 1 hour. Thereafter, PyBOP (1.4 mg, 2.7 µmol) and DIPEA (0.46 µl, 2.7 µmol) were added to the reaction solution, and the obtained mixture was then stirred for 2.5 hours. Thereafter, diethyl ether (5 ml) was added to the reaction solution to precipitate a compound. The precipitated compound was filtrated, and the precipitate was then recovered with a 50% acetonitrile aqueous solution. The recovered product was freeze-dried, and a 95% TFA aqueous solution was added to the obtained freeze-dried product. The obtained mixture was stirred at 25° C. for 2 hours. The resin was removed by filtration. The reaction solution was concentrated and was then dissolved in a 50% acetonitrile aqueous solution, followed by freeze-drying. The freeze-dried product was purified by HPLC (Vydac column C4, 250×4.6 mm; developing solvents A: 0.1% TFA aqueous solution; and B: 0.08% TFA; acetonitrile:water=90:10; gradients A:B=80:20→40:60; 60 minutes; flow rate: 1.0 ml/min) to obtain a 6-residue sugar chain-added peptide having benzylthioester at the C-terminus thereof, Ala-Leu-Leu-Val-Asn(Oligosaccharide chain)-Ser-SBn (SEQ ID NO: 15).

The following method can also be applied as the aforementioned step of obtaining the 6-residue sugar chain-added peptide shown in SEQ ID NO: 15 from the reaction with sugar chain asparagine in an Eppendorf tube:

After washing with DMF, a resin corresponding to 4.3 µmol of 1-residue peptide was transferred into an Eppendorf tube. The sugar chain asparagine (17 mg, 8.6 µmol) represented by Formula (9) and DEPBT (6 mg, 8.6 µmol) were dissolved in DMF:DMSO=4:1 (0.29 mL), and the obtained solution was then placed in an Eppendorf tube. DIPEA (1.5 µl, 8.6 µmol) was added thereto, and the obtained mixture was then stirred at 25° C. for 18 hours.

After completion of the stirring operation, the resin was washed with DCM and DMF. The Fmoc group was treated with a 20% piperidine/DMF solution (1 mL) for 10 minutes for deprotection. After washing with DMF, as for the subsequent elongation of a glycopeptide chain, amino acids were successively condensed according to the below-mentioned method.

An amino acid whose amino group had been protected by an Fmoc group, HOBt (2.9 mg, 0.022 mmol), and DIPCI (3.3 µL, 0.022 mmol) were dissolved in DMF (0.54 mL), and the obtained solution was then activated for 15 minutes. Thereafter, the solution was placed in the solid-phase synthesis column. After stirring at 25° C. for 1 hour, the Fmoc group was treated with a 20% piperidine/DMF solution (1 mL) for 20 minutes for deprotection. These operations were repeated, so that amino acids were successively condensed. As amino acids whose amino groups had been protected by the Fmoc groups, Fmoc-Val (7.3 mg, 0.022 mmol), Fmoc-Leu (7.6 mg, 0.022 mmol), Fmoc-Leu (7.6 mg, 0.022 mmol), and Boc-Ala (4.0 mg, 0.022 mmol) were used, and a 6-residue sugar-added peptide having a protecting group, Boc-Ala-Leu-Leu-Val-Asn(Oligosaccharide chain)-Ser(tBu) (SEQ ID NO: 14), was obtained on the solid-phase resin. Acetic acid:trifluoroethanol (=1:1) was added to this sugar-added peptide to such an extent that the resin was sufficiently immersed therein. Twenty-four hours later, the resin was removed by filtration, and a filtrate portion was then added to diethyl ether, which had been prepared separately to carry out crystallization. Thereafter, the solution portion was removed using a membrane filter, thereby obtaining a residue containing a 6-residue sugar chain-added peptide having a protecting group (SEQ ID NO: 14).

18 mg (7.5 µmol) of the obtained 6-residue sugar chain-added peptide having a protecting group (SEQ ID NO: 14), molecular sieve (MS) 4A (190 mg), and benzylmercaptan (26 µl, 37.5 µmol) were stirred in a DMF solvent (1.9 ml) in an argon atmosphere at −20° C. for 1 hour. Thereafter, PyBOP (20 mg, 37.5 µmol) and DIPEA (6.7 µl, 37.5 µmol) were added to the reaction solution, and the obtained mixture was then stirred for 2 hours. Thereafter, diethyl ether (10 ml) was added to the reaction solution to precipitate a compound. The precipitated compound was filtrated, and the precipitate was then dissolved in DMF. The obtained solution was concentrated under a reduced pressure, and a 95% TFA aqueous solution was added to the obtained residue. The obtained mixture was stirred at 25° C. for 2 hours. The reaction solution was concentrated and was then purified by HPLC (Vydac column C4, 250×4.6 mm; developing solvents A: 0.1% TFA aqueous solution; and B: 0.08% TFA; acetonitrile:water=90:10; gradients A:B=100:0→40:60; 60 minutes; flow rate: 1.0 ml/min) to obtain a 6-residue sugar chain-added peptide having benzylthioester at the C-terminus thereof, Ala-Leu-Leu-Val-Asn(Oligosaccharide chain)-Ser-SBn (SEQ ID NO: 15).

On the other hand, Wang resin (manufactured by Merck) (100 µmol) was placed in a solid-phase synthesis column, and it was then fully washed with methylene chloride (DCM) and DMF. Thereafter, the resultant was fully swollen with DCM. Fmoc-Ala (0.50 mmol), MSNT (0.50 mmol), and N-methylimidazole (0.375 mmol) were dissolved in DCM (2 mL), and the obtained solution was then placed in the solid-phase synthesis column, followed by stirring at 25° C. for 1 hour. It is to be noted that the volume of the DCM can also be set at 1.5 mL. After completion of the stirring operation, the resin was fully washed with DCM and DMF, and the Fmoc group was treated with a 20% piperidine/DMF solution (2 mL) for 15 minutes for deprotection. It is to be noted that the present deprotection treatment can also be carried out for 10 minutes. After washing with DMF, as for the subsequent elongation of a peptide chain, amino acids were successively condensed according to the below-mentioned method.

An amino acid whose amino group had been protected by an Fmoc group, HOBt (67.6 mg, 0.50 mmol), and DIPCI (77.0 µL, 63.1 mg, 0.50 mmol) were dissolved in DMF (1 mL), and the obtained solution was then activated for 15 minutes. Thereafter, the solution was placed in the solid-phase synthesis column. It is to be noted that the volume of the DMF can also be set at 2 mL. After stirring at 25° C. for 1 hour, the Fmoc group was treated with a 20% piperidine/DMF solution (2 mL) for 20 minutes for deprotection. These operations were repeated, so that amino acids were successively condensed. As amino acids protected by the Fmoc groups, Fmoc-Lys (Boc) (234.3 mg, 0.50 mmol), Fmoc-Asp (OtBu) (205.8 mg, 0.50 mmol), Fmoc-Val (169.7 mg, 0.50 mmol), Fmoc-His (Trt) (309.9 mg, 0.50 mmol), Fmoc-Leu (176.7 mg, 0.50 mmol), Fmoc-Gln (184.2 mg, 0.50 mmol), Fmoc-Leu (176.7 mg, 0.50 mmol), Fmoc-Pro (168.7 mg, 0.50 mmol), Fmoc-Glu (OtBu) (212.8 mg, 0.50 mmol), Fmoc-Trp (Boc) (263.3 mg, 0.50 mmol), Fmoc-Pro (168.7 mg, 0.50 mmol), Fmoc-Gln (184.2 mg, 0.50 mmol), and Fmoc-Cys (Trt) (292.9 mg, 0.50 mmol) were used, and a 14-residue peptide having a protecting group, Fmoc-Cys(Trt)-Gln-Pro-Trp(Boc)-Glu(OtBu)-Pro-Leu-Gln-Leu-His(Trt)-Val-Asp(OtBu)-Lys(Boc)-Ala (SEQ ID NO: 16), was obtained on the solid-phase resin. Thereafter, the Fmoc group was treated with a 20% piperidine/DMF solution (2 mL) for 20 minutes for deprotection, the resultant was then washed with DMF and DCM. Thereafter, a previously prepared reagent K (TFA/water/phenol/thioanisole/EDT=82.5/5/5/5/2.5) was added to such an extent that the resin was sufficiently immersed therein, and it was then stirred at 25° C. for 2 hours. It is to be noted that, instead of the reagent K, TFA/water/phenol/thioanisole/EDT/TIPS=81.5/5/5/5/2.5/1.0 may also be used. The resin was removed by filtration, and the reaction solution was then concentrated under a reduced pressure. The obtained residue was purified by HPLC (Vydac column C8, 250×10 mm; developing solvents A: 0.1% TFA aqueous solution; and B: 0.08% TFA; acetonitrile:water=90:10; gradients A:B=80:20→40:60; 30 minutes; flow rate: 4.0 ml/min) to obtain a 14-residue peptide, Cys-Gln-Pro-Trp-Glu-Pro-Leu-Gln-Leu-His-Val-Asp-Lys-Ala (SEQ ID NO: 17).

1.1 mg of the thus prepared 14-residue peptide (SEQ ID NO: 17) and 1.3 mg of the previously synthesized 6-residue sugar-added peptide having benzylthioester at the C-terminus thereof (SEQ ID NO: 15) were placed in a single Eppendorf tube, and they were dissolved in 275 µL of a phosphate buffer (pH 7.2; containing 6 M guanidine hydrochloride). Thereafter, thiophenol (1 µL) and benzylmercaptan (1 µL) were added to the solution at 25° C., and a reaction was then carried out at 37° C. Twenty-six hours later, after confirming by HPLC that the reaction had been terminated, the reaction solution was purified by HPLC (Vydac column C18, 250×4.6 mm; developing solvents A: 0.1% TFA aqueous solution; and B: 0.08% TFA; acetonitrile:water=90:10; gradients A:B=80:20→50:50; 60 minutes; flow rate: 1.0 ml/min) to obtain 1.5 mg of a 20-residue sugar chain-added peptide, Ala-Leu-Leu-Val-Asn(Oligosaccharide chain)-Ser-Cys-Gln-Pro-Trp-Glu-Pro-Leu-Gln-Leu-His-Val-Asp-Lys-Ala (SEQ ID NO: 18).

1.5 mg (0.39 µmol) of the obtained 20-residue sugar chain-added peptide (SEQ ID NO: 18) was placed in a round-bottom flask, and it was dissolved in 0.39 mL of a 0.25 M Tris-HCl buffer (pH 8.6; containing 6 M guanidine hydrochloride solution and 3.3 mM EDTA) and 0.13 mL of acetonitrile. Thereafter, methyl-4-nitrobenzenesulfonate (1.7 mg) was added to the solution at 25° C. Forty minutes later, a 10% TFA solution (1.5 mL) was added thereto, so that the pH of the solution was adjusted to be pH 4. Thereafter, diethyl ether was added thereto to carry out an extraction operation. After a water layer had been concentrated, the obtained residue was purified by HPLC (Vydac column C4, 250×4.6 mm; developing solvents A: 0.1% TFA aqueous solution; and B: 0.08% TFA; acetonitrile:water=90:10; gradients A:B=80:20→55:45; 60 minutes; flow rate: 1.0 ml/min) (wherein a C18 column can also be used in the purification, instead of the aforementioned C4 column) to obtain 1.6 mg of a 20-residue sugar chain-added peptide, Ala-Leu-Leu-Val-Asn(Oligosaccharide chain)-Ser-Cys(Me)-Gln-Pro-Trp-Glu-Pro-Leu-Gln-Leu-His-Val-Asp-Lys-Ala (SEQ ID NO: 19), wherein the sulfur atom of the cysteine residue was methylated.

ESI-MS: Calcd for $C_{165}H_{265}N_{31}O_{74}S$: $[M+2H]^{2+}$ 1300.7. Found, 1300.4

1.6 mg (0.4 µmol) of the obtained 20-residue sugar chain-added peptide (SEQ ID NO: 19) wherein the sulfur atom of the cysteine residue had been methylated was placed in an Eppendorf tube, and it was dissolved in 0.4 mL of a 80% formic acid solution. Thereafter, 4.3 mg (0.04 mmol) of cyanogen bromide was added to the solution at 25° C. The reactor was shaded from light, and a reaction was then carried out at 37° C. Thirty-five hours later, the reaction solution was frozen to terminate the reaction. A 5% hydrazine hydrate (200 µL) was added to the residue obtained after the freeze-drying of the reaction solution, and the inside of the reaction system was adjusted to be pH 10 to 11. Five minutes later, acetic acid (5 µL) was added to the reaction system, so that the inside thereof was adjusted to pH 8 to 9. The resultant was purified by HPLC (Vydac column C4, 250×4.6 mm; developing solvents A: 0.1% TFA aqueous solution; and B: 0.08% TFA; acetonitrile:water=90:10; gradients A:B=80:20→50:50; 30 minutes; flow rate: 1.0 ml/min) to obtain 0.7 mg of a 20-residue sugar chain-added peptide, Ala-Leu-Leu-Val-Asn(Oligosaccharide chain)-Ser-Ser-Gln-Pro-Trp-Glu-Pro-Leu-Gln-Leu-His-Val-Asp-Lys-Ala (SEQ ID NO: 20), which was a glycopeptide of interest.

Thirty-four hours after a reaction with cyanogen bromide, the reaction solution was concentrated under a reduced pressure, and a 5% hydrazine hydrate (200 µL) was added to the obtained residue, followed by stirring for 10 minutes. Thereafter, 5 µL of acetic acid was added to the reaction solution, and the obtained mixture was then purified by HPLC. In this case also, the same 20-residue sugar chain-added peptide (SEQ ID NO: 20) could be obtained.

ESI-MS: Calcd for $C_{164}H_{263}N_{31}O_{75}$: $[M+2H]^{2+}$ 1290.6. Found, 1290.7

Example 5

Production of Ac-Gly-Ser-Gly-Met-Ala

Wang resin (manufactured by Merck) (100 µmol) was placed in a solid-phase synthesis column, and it was then fully washed with methylene chloride (DCM) and DMF. Thereafter, the resultant was fully swollen with DCM. Fmoc-Ala (0.50 mmol), MSNT (0.50 mmol), and N-methylimidazole (0.375 mmol) were dissolved in DCM (1.5 mL), and the obtained solution was then placed in the solid-phase synthesis column, followed by stirring at 25° C. for 2 hours. After completion of the stirring operation, the resin was fully washed with DCM and DMF, and the Fmoc group was treated with a 20% piperidine/DMF solution (2 mL) for 15 minutes for deprotection. After washing with DMF, as for the subsequent elongation of a peptide chain, amino acids were successively condensed according to the below-mentioned method.

An amino acid whose amino group had been protected by an Fmoc group, HOBt (67.6 mg, 0.50 mmol), and DIPCI (77.0 µL, 63.1 mg, 0.50 mmol) were dissolved in DMF (2 mL), and the obtained solution was then activated for 15 minutes. Thereafter, the solution was placed in the solid-phase synthesis column. After stirring at 25° C. for 1 hour, the Fmoc group was treated with a 20% piperidine/DMF solution (2 mL) for 10 minutes for deprotection. These operations were repeated, so that amino acids were successively condensed. As amino acids protected by the Fmoc groups, Fmoc-Met(0) (193.8 mg, 0.50 mmol), Fmoc-Gly (148.9 mg, 0.50 mmol), Fmoc-Cys(Trt) (292.9 mg, 0.50 mmol), and Fmoc-Gly (148.9 mg, 0.50 mmol) were used, and a 5-residue peptide having a protecting group, Fmoc-Gly-Cys(Trt)-Gly-Met(O)-Ala (SEQ ID NO: 21), was obtained on the solid-phase resin. Thereafter, the Fmoc group was treated with a 20% piperidine/DMF solution (2 mL) on the resin for 10 minutes for deprotection, and free amino groups were then protected by acetyl using a 20% acetic anhydride/DMF solution (1.25 mL). After washing with DMF and DCM, a previously prepared reagent (TFA/water/TIPS=95/2.5/2.5) was added to such an extent that the resin was sufficiently immersed therein, and it was then stirred at 25° C. for 2 hours. The resin was removed by filtration, and 20 mL of diethyl ether was then added to the filtrate for precipitation. The precipitate was filtrated, and the filtrate was then dissolved in a 0.1% TFA aqueous solution. The obtained solution was concentrated under a reduced pressure, and the resultant was then freeze-dried to obtain a mixture comprising a 5-residue peptide, Ac-Gly-Cys-Gly-Met(O)-Ala (SEQ ID NO: 22), wherein the sulfur atom of the methionine at position 4 was oxidized.

5 mg of the obtained 5-residue peptide (SEQ ID NO: 22) mixture, wherein the sulfur atom of the methionine at position 4 had been oxidized, was placed in a round-bottom flask, and it was dissolved in 10 mL of a 0.25 M Tris-HCl buffer (pH 8.6; containing 6 M guanidine hydrochloride solution and 3.3 mM EDTA). 2-mercaptoethanol (7 μL) was added to the obtained solution, and the obtained mixture was then stirred for 10 minutes. Thereafter, 3.3 mL of an acetonitrile solution containing methyl-4-nitrobenzenesulfonate (66 mg) was added to the reaction solution. Twenty-five minutes later, a 10% TFA solution (1.0 mL) was added thereto for neutralization. Thereafter, diethyl ether was added thereto to carry out an extraction operation 3 times. After a water layer had been concentrated under a reduced pressure, the obtained residue was purified by HPLC (Vydac column C18, 250×10 mm; developing solvents A: 0.1% TFA aqueous solution; and B: 0.09% TFA; acetonitrile:water=90:10; gradients A:B=100:0→100:0→60:40; 0 minute→5 minutes→35 minutes; flow rate: 4.0 ml/min) to obtain 4 mg of a 5-residue peptide, Ac-Gly-Cys(Me)-Gly-Met(O)-Ala (SEQ ID NO: 23), wherein the sulfur atom of the cysteine residue at position 2 was methylated and the methionine residue at position 4 was oxidized.

3.8 mg of the obtained 5-residue peptide (SEQ ID NO: 23), wherein the sulfur atom of the cysteine residue at position 2 had been methylated and the methionine residue at position 4 had been oxidized, was placed in an Eppendorf tube, and it was dissolved in 3.1 mL of a 80% formic acid solution. Thereafter, 79.0 mg of cyanogen bromide was added to the solution, and the reactor was then shaded from light. The reaction solution was stirred under argon-substituted conditions at 37° C. for 39 hours. After completion of the reaction, the resultant was subjected to vacuum concentration to obtain a residue containing an ester form as a reaction intermediate.

The obtained residue was placed in an Eppendorf tube, and it was dissolved in 1.25 mL of a sodium phosphate buffer (containing 6 M guanidine hydrochloride; pH 7.2), followed by stirring for 45 minutes. Thereafter, 3.6 mL of trifluoroacetic acid, 22 mg of ammonium iodide, and 11 μL of dimethyl sulfide were added to the reaction solution, and the obtained mixture was then stirred at a room temperature. Thirty minutes later, 10 mL of water was added to the reaction solution, and the obtained solution was then separated and washed with carbon tetrachloride. A water layer was concentrated under a reduced pressure, and the obtained residue was then purified by HPLC (Vydac column C18, 250×4.6 mm; developing solvents A: 0.1% TFA aqueous solution; and B: 0.09% TFA; acetonitrile:water=90:10; gradients A:B=100:0→100:0→60:40; 0 minute→5 minutes→65 minutes; flow rate: 1.0 ml/min) to obtain 2.6 mg of a 5-residue peptide of interest having a protecting group, Ac-Gly-Ser-Gly-Met-Ala (SEQ ID NO: 24).

ESI-MS: Calcd for $C_{16}H_{28}N_4O_7$: $[M+1H]^{1+}$ 464.2. Found, 464.5

Example 6

Production of Ser-Thr(GalNAc)-Ala-Pro-Pro-Ala-His-Gly-Val-Thr-Ser-Ala-Pro-Asp-Thr-Arg-Pro-Ala-Pro-Gly-Ser-Thr(GalNAc)-Ala-Pro-Pro-Ala-His-Gly-Val-Thr-Ser-Ala-Pro-Asp-Thr-Arg-Pro-Ala-Pro-Gly Amino-PEGA resin (manufactured by Merck) (100 μmol) was placed in a solid-phase synthesis column, and it was then fully washed with methylene chloride (DCM) and DMF. Thereafter, the resultant was fully swollen with DMF. 4-hydroxymethyl-3-methoxyphenoxy butyric acid (HMPB) (0.25 mmol), TBTU (0.25 mmol), and N-ethylmorpholine (0.25 mmol) were dissolved in DMF (2 mL), and the obtained solution was then placed in the column, followed by stirring at 25° C. for 2 hours. Thereafter, the resin was fully washed with DMF and DCM to obtain an HMPB-PEGA resin. The obtained HMPB-PEGA resin was used as a solid-phase carrier in solid-phase synthesis.

Fmoc-Gly (0.50 mmol), MSNT (0.50 mmol), and N-methylimidazole (0.375 mmol) were dissolved in DCM (4.5 ml), and the obtained solution was then placed in the solid-phase synthesis column, followed by stirring at 25° C. for 3 hours. After completion of the stirring operation, the resin was washed with DCM and DMF, and the Fmoc group was treated with a 20% piperidine/DMF solution (2 mL) for 10 minutes for deprotection. After washing with DMF, as for the subsequent elongation of a peptide chain, amino acids were successively condensed according to the below-mentioned method.

An amino acid whose amino group had been protected by an Fmoc group, HOBt (67.6 mg, 0.50 mmol), and DIPCI (77.0 μL, 63.1 mg, 0.50 mmol) were dissolved in DMF (4 mL), and the obtained solution was then activated for 15 minutes. Thereafter, the solution was placed in the solid-phase synthesis column. After stirring at 25° C. for 1 hour, the Fmoc group was treated with a 20% piperidine/DMF solution (2 mL) for 10 minutes for deprotection. These operations were repeated, so that amino acids were successively condensed. As amino acids protected by the Fmoc groups, Fmoc-Pro, Fmoc-Ala, Fmoc-Pro, Fmoc-Arg (Pbf), Fmoc-Thr (tBu), Fmoc-Asp (OtBu), Fmoc-Pro, Fmoc-Ala, Fmoc-Ser (tBu), Fmoc-Thr (tBu), Fmoc-Val, Fmoc-Gly, Fmoc-His (Trt), Fmoc-Ala, Fmoc-Pro, Fmoc-Pro, and Fmoc-Ala were used. On the solid-phase resin, a 18-residue peptide having a protecting group, Fmoc-Ala-Pro-Pro-Ala-His(Trt)-Gly-Val-Thr(tBu)-Ser(tBu)-Ala-Pro-Asp(OtBu)-Thr(tBu)-Arg(Pbf)-Pro-Ala-Pro-Gly (SEQ ID NO: 25), was obtained.

This 18-residue peptide having a protecting group (SEQ ID NO: 25) was treated with a 20% piperidine/DMF solution (2 mL) on the resin for 10 minutes for deprotection of the Fmoc group. After the resultant had been washed with DMF and DCM, Fmoc-Thr(GalNAc) (0.20 mmol), HOBt (0.50 mmol), and DIPCI (0.50 mmol) that had been dissolved in DMF (3.6 mL) and had been activated for 15 minutes were added to the resultant. After the reaction for 5 hours, the Fmoc group was treated with a 20% piperidine/DMF solution (2 mL) for 20 minutes for deprotection to obtain a 19-residue sugar-added peptide having a protecting group, Thr(GalNAc)-Ala-Pro-Pro-Ala-His(Trt)-Gly-Val-Thr(tBu)-Ser(tBu)-Ala-Pro-Asp(OtBu)-Thr(tBu)-Arg(Pbf)-Pro-Ala-Pro-Gly (SEQ ID NO: 26), on the solid-phase resin.

0.02 mmol out of the obtained 19-residue sugar-added peptide having a protecting group (SEQ ID NO: 26) on the solid-phase resin was transferred into another solid-phase synthesis column. Boc-Ser(tBu) (0.1 mmol), DIPCI (0.1 mmol), and HOBt (0.1 mmol) that had been dissolved in 0.5 mL of DMF and had been activated for 15 minutes were added to the column, and a reaction was then carried out for 1 hour. Thereafter, the reaction solution was filtrated, and acetic acid:trifluoroethanol=1:1 were added thereto to such an extent that the resin was sufficiently immersed therein. Fourteen hours later, the resin was removed by filtration, and the filtrate was then concentrated under a reduced pressure to obtain a residue containing a 20-residue sugar-added peptide having a protecting group, Boc-Ser(tBu)-Thr(GalNAc)-Ala-Pro-Pro-Ala-His(Trt)-Gly-Val-Thr(tBu)-Ser(tBu)-Ala-Pro-Asp(OtBu)-Thr(tBu)-Arg(Pbf)-Pro-Ala-Pro-Gly (SEQ ID NO: 27).

75 mg (35 µmol) of the obtained 20-residue sugar-added peptide having a protecting group (SEQ ID NO: 27) and 123 µl (105 µmol) of benzylmercaptan were added to 3.5 ml of DMF, and the obtained mixture was then stirred in an argon atmosphere at −20° C. for 1 hour. Thereafter, PyBOP (91 mg, 175 µmol) and DIPEA (30 µl, 175 µmol) were added to the reaction solution, and the obtained mixture was then stirred for 2.5 hours. Thereafter, diethyl ether was added to the reaction solution to precipitate crystals, followed by filtration. TFA/water/TIPS=95/2.5/2.5 was added to the obtained residue to such an extent that the resin was sufficiently immersed therein, and the obtained mixture was then stirred at 25° C. for 2 hours. The resin was removed by filtration, and the filtrate was then concentrated, so that the obtained residue was recovered. The obtained residue was purified by HPLC (Vydac column C8, 250×10 mm; developing solvents A: 0.1% TFA aqueous solution; and B: 0.09% TFA; acetonitrile:water=90:10; gradients A:B=90:10→60:40; 30 minutes; flow rate: 4.0 ml/min) to obtain a 20-residue sugar-added peptide having benzylthioester at the C-terminus thereof, Ser-Thr(GalNAc)-Ala-Pro-Pro-Ala-His-Gly-Val-Thr-Ser-Ala-Pro-Asp-Thr-Arg-Pro-Ala-Pro-Gly-SBn (SEQ ID NO: 28).

On the other hand, 0.02 mmol out of the previously obtained 19-residue sugar-added peptide having a protecting group (SEQ ID NO: 26) on the solid-phase resin was transferred into another solid-phase synthesis column. Boc-Thia (0.04 mmol), DIPCI (0.1 mmol), and HOBt (0.1 mmol) that had been dissolved in 1.5 mL of DMF and had been activated for 15 minutes were added to the column, and a reaction was then carried out for 20 minutes. Thereafter, the reaction solution was filtrated, and a reagent (TFA/water/TIPS=95/2.5/2.5) was added thereto to such an extent that the resin was sufficiently immersed therein. The obtained mixture was stirred at 25° C. for 2 hours. The resin was removed by filtration, and the filtrate was then concentrated. The obtained residue was dissolved in 2.1 ml of 0.2 M methoxyamine and 0.1 M sodium phosphate buffer (pH 4; containing 6 M guanidine hydrochloride), so that the thiazoline at the N-terminus was subjected to ring-opening. Thereafter, the reaction solution was purified by HPLC (Vydac column C8, 250×10 mm; developing solvents A: 0.1% TFA aqueous solution; and B: 0.08% TFA; acetonitrile:water=90:10; gradients A:B=90:10→60:40; 30 minutes; flow rate: 4.0 ml/min) to obtain a 20-residue sugar-added peptide, Cys-Thr(GalNAc)-Ala-Pro-Pro-Ala-His-Gly-Val-Thr-Ser-Ala-Pro-Asp-Thr-Arg-Pro-Ala-Pro-Gly (SEQ ID NO: 29).

13 mg of the thus obtained 20-residue sugar-added peptide (SEQ ID NO: 29) and 12 mg of the previously obtained 20-residue peptide having benzylthioester at the C-terminus thereof (SEQ ID NO: 28) were dissolved in 2.9 mL of a phosphate buffer (pH 7.2; containing 6 M guanidine hydrochloride). Thereafter, 30 mg of 4-mercaptophenylacetic acid and 17 mg of tris(2-carboxyethyl)phosphine were added to the above solution, and a reaction was then carried out for 3 hours. The reaction solution was purified by HPLC (Vydac column C8, 250×10 mm; developing solvents A: 0.1% TFA aqueous solution; and B: 0.09% TFA; acetonitrile:water=90:10; gradients A:B=90:10→60:40; 30 minutes; flow rate: 4.0 ml/min) to obtain 18 mg of a 40-residue sugar-added peptide, Ser-Thr(GalNAc)-Ala-Pro-Pro-Ala-His-Gly-Val-Thr-Ser-Ala-Pro-Asp-Thr-Arg-Pro-Ala-Pro-Gly-Cys-Thr(GalNAc)-Ala-Pro-Pro-Ala-His-Gly-Val-Thr-Ser-Ala-Pro-Asp-Thr-Arg-Pro-Ala-Pro-Gly (SEQ ID NO: 30).

16 mg of the obtained 40-residue sugar-added peptide (SEQ ID NO: 30) was placed in a round-bottom flask, and it was dissolved in 3.8 mL of a 0.25 M Tris-HCl buffer (pH 8.6; containing 6 M guanidine hydrochloride solution and 3.3 mM EDTA). Thereafter, 2-mercaptoethanol (3 µL) was added to the obtained solution, and the obtained mixture was then stirred for 10 minutes. Subsequently, 1.27 mL of acetonitrile containing 25 mg of methyl-4-nitrobenzenesulfonate was added to the reaction solution. Twenty-five minutes later, 0.45 mL of a 10% TFA solution was added to the reaction solution for neutralization, and 2 mL of diethyl ether was then added thereto, followed by separation and washing 3 times. After a water layer had been concentrated under a reduced pressure, the obtained residue was purified by HPLC (Vydac column C-4, 250×4.6 mm; developing solvents A: 0.1% TFA aqueous solution; and B: 0.08% TFA; acetonitrile:water=90:10; gradients A:B=100:0→100:0→90:10→60:40; 0 minute→10 minutes→40 minutes; flow rate: 1.2 ml/min) to obtain 13 mg of a mixture comprising a 40-residue sugar-added peptide, Ser-Thr(GalNAc)-Ala-Pro-Pro-Ala-His-Gly-Val-Thr-Ser-Ala-Pro-Asp-Thr-Arg-Pro-Ala-Pro-Gly-Cys(Me)-Thr(GalNAc)-Ala-Pro-Pro-Ala-His-Gly-Val-Thr-Ser-Ala-Pro-Asp-Thr-Arg-Pro-Ala-Pro-Gly (SEQ ID NO: 31), wherein the sulfur atom of the cysteine residue at position 21 was methylated.

12 mg of the obtained mixture comprising the 40-residue sugar-added peptide (SEQ ID NO: 31), wherein the sulfur atom of the cysteine residue at position 21 had been methylated, was placed in a round-bottom flask, and it was dissolved in 2.9 mL of a 80% formic acid aqueous solution. Thereafter, 152 mg of cyanogen bromide was added to the solution at 25° C. The reactor was shaded from light, and a reaction was then carried out at 37° C. Thirty-six hours later, the reaction solution was concentrated under a reduced pressure. The residue was dissolved in 2.9 mL of trifluoroacetic acid, and thereafter, 2.4 mg of ammonium iodide and 24 µL of dimethyl sulfide were added thereto, followed by a reaction at a room temperature for 30 minutes. Thirty minutes later, 6 mL of water was added to the reaction system, and separation and washing were then carried out using carbon tetrachloride. A water layer was concentrated under a reduced pressure, and the residue was then dissolved in 1.4 mL of a 5% hydrazine aqueous solution, followed by a reaction at a room temperature for 10 minutes. Ten minutes later, 0.14 mL of acetic acid was added to the reaction solution, and the obtained mixture was then purified by HPLC (Vydac column C-4, 250×4.6 mm; developing solvents A: 50 mM AcONH4 aqueous solution; and B: acetonitrile; gradients A:B=90:10→70:30; 60 minutes; flow rate: 1.0 ml/min) to obtain 2.3 mg of a 40-residue sugar-added peptide of interest, Ser-Thr(GalNAc)-Ala- Pro-Pro-Ala-His-Gly-Val-Thr-Ser-Ala-Pro-Asp-Thr-Arg-Pro-Ala-Pro-Gly-Ser-Thr(GalNAc)-Ala-Pro-Pro-Ala-His-Gly-Val-Thr-Ser-Ala-Pro-Asp-Thr-Arg-Pro-Ala-Pro-Gly (SEQ ID NO: 32).

ESI-MS: Calcd for: $[M+3H]^{3+}$ 1388.5. Found, 1388.6

Example 7

Production of Glu-Ser-Asn-Gly-Thr-Leu-Thr-Leu

Trt chloride resin (manufactured by Merck) (100 μmol) was placed in a solid-phase synthesis column, and it was then fully washed with methylene chloride (DCM) and DMF. Thereafter, the resultant was fully swollen with DCM. After filtration, Fmoc-Gly (0.20 mmol) and DIPEA (0.4 mmol) were dissolved in DCM (0.66 mL), and the obtained solution was then placed in the solid-phase synthesis column, followed by stirring at 25° C. for 2 hours. After completion of the stirring operation, the resin was sufficiently washed with DCM:MeOH:DIPEA=17: 2:1, DCM, and DMF, and the Fmoc group was treated with a 20% piperidine/DMF solution (1 mL) for 20 minutes for deprotection. After washing with DMF, as for the subsequent elongation of a peptide chain, amino acids were successively condensed according to the below-mentioned method.

An amino acid whose amino group had been protected, HOBt (67.6 mg, 0.50 mmol), and DIPCI (77.0 μL, 63.1 mg, 0.50 mmol) were dissolved in DMF (2 mL), and the obtained solution was then activated for 15 minutes. Thereafter, the solution was placed in the solid-phase synthesis column. After stirring at 25° C. for 1 hour, the Fmoc group was treated with a 20% piperidine/DMF solution (2 mL) for 20 minutes for deprotection. These operations were repeated, so that amino acids were successively condensed. As the protected amino acids, Fmoc-Asn (177.2 mg, 0.50 mmol), Fmoc-Ser (tBu) (191.6 mg, 0.50 mmol), and Boc-Glu(OtBu) (151.6 mg, 0.50 mmol) were used. On the solid-phase resin, a 4-residue peptide having a protecting group, Boc-Glu(OtBu)-Ser(tBu)-Asn-Gly (SEQ ID NO: 33), was obtained.

After the resultant had been washed with DMF and DCM, 2 mL of AcOH:MeOH:DCM=5:4:1 was added thereto, followed by a reaction at a room temperature for 2 hours. Two hours later, the reaction solution was recovered by filtration, and it was then concentrated under a reduced pressure to obtain a residue. 1 mL of benzene was added to this residue, an azeotropic operation was then carried out thereon 2 times, and the resultant was then dissolved in 0.81 mL of DMF. To the obtained solution, 42.1 mg of PyBOP, 14 μl of DIPEA, and 57 μl of benzylmercaptan were added in an argon atmosphere at 0° C., and the obtained mixture was then stirred for 30 minutes. After completion of the reaction, the reaction solution was neutralized with a saturated ammonium chloride aqueous solution, and it was then separated and washed with water and a saturated saline. An organic layer was dried over magnesium sulfate, and it was then filtered. Thereafter, the filtrate was concentrated under a reduced pressure. The obtained residue was purified by silica gel column chromatography (developing solvents; ethyl acetate:MeOH:water=20:2:1) to gather fractions containing peptides of interest, and the gathered fractions were then concentrated under a reduced pressure. The obtained residue was dissolved in a 95% TFA aqueous solution, and a reaction was then carried out for 10 minutes. The reaction solution was concentrated under a reduced pressure to obtain a 4-residue peptide having benzylthioester at the C-terminus thereof, Glu-Ser-Asn-Gly-SBn (SEQ ID NO: 34).

On the other hand, Wang resin (manufactured by Merck) (0.1 mmol) was placed in a solid-phase synthesis column, and it was then fully washed with methylene chloride (DCM) and DMF. Thereafter, the resultant was fully swollen with DCM. Fmoc-Leu (0.50 mmol), MSNT (0.50 mmol), and N-methylimidazole (0.375 mmol) were dissolved in DCM (2 mL), and the obtained solution was then placed in the solid-phase synthesis column, followed by stirring at 25° C. for 2 hours. Two hours later, the resin was fully washed with DCM and DMF, and the Fmoc group was treated with a 20% piperidine/DMF solution (2 mL) for 20 minutes for deprotection. After washing with DMF and DCM, as for the subsequent elongation of a peptide chain, amino acids were successively condensed according to the below-mentioned method.

An amino acid whose amino group had been protected, HOBt (67.6 mg, 0.50 mmol), and DIPCI (77.0 μL, 0.50 mmol) were dissolved in 2 mL of DMF, and the obtained solution was then activated for 15 minutes. Thereafter, the solution was placed in the solid-phase synthesis column. After stirring at 25° C. for 1 hour, the Fmoc group was treated with a 20% piperidine/DMF solution (2 mL) for 20 minutes for deprotection. These operations were repeated, so that amino acids were successively condensed. As the protected amino acids, Fmoc-Thr(tBu) (198.8 mg, 0.50 mmol) and Fmoc-Leu (176.8 mg, 0.50 mmol) were used, and a 3-residue peptide having a protecting group, Fmoc-Leu-Thr(tBu)-Leu, was obtained on the solid-phase resin. Thereafter, the Fmoc group was treated with a 20% piperidine/DMF solution (2 mL) for 20 minutes for deprotection. Then, a threonine derivative having a protecting group, Boc-Thr(S-SsecBu) synthesized in Synthesis Example 1 separately, HOBt (67.6 mg, 0.50 mmol), and DIPCI (77.0 μL, 0.50 mmol) that had been dissolved in 2 mL of DMF and had been then activated for 15 minutes were added to the solution. The obtained mixture was then reacted for 3 hours to obtain a 4-residue peptide having a protecting group, Boc-Thr(S-SsecBu)-Leu-Thr(tBu)-Leu (SEQ ID NO: 35), on the solid-phase resin. A 95% TFA aqueous solution was added to the aforementioned 4-residue peptide, and a reaction was then carried out at a room temperature for 2 hours. Thereafter, the resin was removed by filtration, and the filtrate was then concentrated under a reduced pressure to obtain a 4-residue peptide having a protecting group, Thr(S-SsecBu)-Leu-Thr-Leu (SEQ ID NO: 36).

2.2 mg of the thus obtained 4-residue peptide having a protecting group (SEQ ID NO: 36) and 2.2 mg of the previously obtained 4-residue peptide having thioester (SEQ ID NO: 34) were dissolved in xx mL of a 0.2 M sodium phosphate buffer (pH 7.3; containing 6 M guanidine hydrochloride and 20 mg of 4-mercaptophenylacetic acid), followed by a reaction for 3.5 hours. After completion of the reaction, dithiothreitol was added to the reaction solution, and the obtained mixture was then stirred for 10 minutes. Thereafter, the reaction solution was purified by HPLC (Cadenza column C18, 75×4.6 mm; developing solvents A: 0.1% TFA aqueous solution; and B: 0.1% TFA; acetonitrile:water=90:10; gradients A:B=90:10→35:65; 15 minutes; flow rate: 1.0 ml/min) to obtain a 8-residue peptide, Glu-Ser-Asn-Gly-Thr(SH)-Leu-Thr-Leu (SEQ ID NO: 37), wherein the side chain hydroxyl group of the threonine residue at position 5 was substituted with a thiol group. The threonine derivative residue contained in the obtained peptide was considered to have a configuration mainly represented by the following formula:

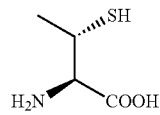

3.5 mg of the obtained 8-residue peptide (SEQ ID NO: 37), wherein the side chain hydroxyl group of the threonine residue at position 5 had been substituted with a thiol group, was placed in a round-bottom flask, and it was dissolved in 4.1 mL of a 0.25 M Tris-HCl buffer (pH 8.6; containing 6 M guanidine hydrochloride solution and 3.3 mM EDTA). Thereafter, 2-mercaptoethanol (2.9 μL) was added to the obtained solution, and the obtained mixture was then stirred for 15 minutes. Subsequently, 1.37 mL of acetonitrile, in which methyl-4-nitrobenzenesulfonate (26.2 mg) had been dissolved, was added to the reaction solution, and a reaction was then carried out for 50 minutes. After completion of the reaction, a 10% TFA solution (1.0 mL) was added to the reaction solution for neutralization, and the reaction solution was then purified by HPLC (Cadenza column C18, 75×4.6 mm; developing solvents A: 0.1% TFA aqueous solution; and B: 0.1% TFA; acetonitrile:water=90:10; gradients A:B=90:10→35:65; 15 minutes; flow rate: 1.0 ml/min) to obtain a 8-residue peptide, Glu-Ser-Asn-Gly-Thr(SMe)-Leu-Thr-Leu (SEQ ID NO: 38), wherein the sulfur atom of the substituted thiol group of the threonine residue at position 5 was methylated.

4 mg of the obtained 8-residue peptide (SEQ ID NO: 38), wherein the sulfur atom of the substituted thiol group of the threonine residue at position 5 had been methylated, was placed in a round-bottom flask, and it was dissolved in 4.63 mL of a 70% formic acid aqueous solution. Thereafter, 49.0 mg of cyanogen bromide was added to the solution, and the obtained mixture was then stirred under shaded conditions in an argon-substituted atmosphere at 37° C. Forty-eight hours later, the reaction solution was concentrated under a reduced pressure, and 0.93 mL of a 5% hydrazine aqueous solution was then added thereto, followed by a reaction for 15 minutes. 60 μL of acetic acid was added to the reaction solution, and the reaction solution was then purified by HPLC (Cadenza column C18, 75×4.6 mm; developing solvents A: 0.1% TFA aqueous solution; and B: 0.1% TFA; acetonitrile:water=90:10; gradients A:B=85:15→45:55; 15 minutes; flow rate: 1.0 ml/min) to obtain a 8-residue peptide of interest, Glu-Ser-Asn-Gly-Thr-Leu-Thr-Leu (SEQ ID NO: 39). It was assumed from the reaction mechanism that the configuration of the threonine residues contained in the obtained peptide would be the same as that of a natural one.

ESI-MS: Calcd for $C_{34}H_{59}N_9O_{15}$: $[M+1H]^{1+}$ 834.41. Found, 835.1

Synthesis Example 1

Synthesis of Boc-Thr(S-SsecBu)

Boc-Thr (300 mg, 1.37 mmol) was dissolved in distilled DMF (6.85 mL, 200 mM), and N-(3-dimethylaminopropyl)-N'-ethylcarbodiimide hydrochloride (786 mg, 4.1 mmol) and HOBt (370 mg, 2.74 mmol) were then added to the solution. The obtained mixture was stirred at 0° C. for 15 minutes. Thereafter, TMSEtOH (1.95 mL, 13.7 mmol) was added to the reaction solution, and the obtained mixture was then stirred at 0° C. Twenty hours later, after confirming the termination of the reaction by TLC, the reaction solution was diluted with ethyl acetate, and it was then neutralized with a saturated sodium bicarbonate solution. The solution was then separated and washed with water twice, and with a saturated saline once. An organic layer was dried over magnesium sulfate, and was then filtered. The filtrate was concentrated under a reduced pressure. The residue was purified by silica gel column chromatography (developing solvent; ethyl acetate:hexane=1:3) to obtain a Boc-Thr-TMS ester (yield: 342 mg, yield constant: 78%).

The obtained Boc-Thr-TMS ester was subjected to azeotropy with benzene 2 times, and the residue was then dissolved in 20.8 mL of DCM. 322 mL (4.16 mmol) of methanesulfonyl chloride and 1.16 mL (8.32 mmol) of triethylamine were added to the solution, and the obtained mixture was then stirred at 0° C. Ten minutes later, after confirming the termination of the reaction by TLC, the reaction solution was diluted with DCM, and it was then neutralized with a saturated ammonium chloride aqueous solution. Thereafter, the solution was separated and washed with water twice, and with a saturated saline once. An organic layer was dried over magnesium sulfate, and was then filtered. The filtrate was concentrated under a reduced pressure. The residue was purified by silica gel column chromatography (developing solvent; ethyl acetate:hexane=1:4) to obtain a Boc-Thr(OMs)-TMS ester (yield amount: 724.6 mg, yield percentage: 88%).

1.06 g of the obtained Boc-Thr(OMs)-TMS ester was subjected to azeotropy with benzene 2 times, and it was then dried with a desiccator overnight. The resultant was dissolved in 8.9 mL of DMF. Thereafter, a solution obtained by dissolving 0.57 mL (7.95 mmol) of thioacetic acid and 0.79 mL (5.3 mmol) of DBU in 4.4 mL of DMF followed by a reaction for 20 minutes was added to the above solution. The obtained mixture was stirred at 45° C. Eighteen hours later, after confirming the termination of the reaction by TLC, the reaction solution was neutralized with a saturated ammonium chloride aqueous solution, and it was then separated and washed with water twice, and with a saturated saline once. An organic layer was dried over magnesium sulfate, and was then filtrated. The filtrate was concentrated under a reduced pressure. The residue was purified by silica gel column chromatography (developing solvent; ethyl acetate:hexane=1:20) to obtain a Boc-Thr(SAc)-TMS ester (yield amount: 536.8 mg, yield percentage: 53.7%).

1.1 g of the obtained Boc-Thr(SAc)-TMS ester was dissolved in 100 mL of methanol, and thereafter, a solution obtained by dissolving dipyridyl disulfide (3.21 g, 14.6 mmol) and 1.75 mL (16.1 mmol) of Sec-BuSH in 5.5 mL of methanol was added to the above solution. Thereafter, 11.7 mL of a methanol solution of sodium hydroxide (500 mM) was added thereto. Eighteen hours later, after confirming the termination of the reaction by TLC, the reaction solution was neutralized with a 1% acetic acid aqueous solution, it was then concentrated under a reduced pressure, and it was then diluted with ethyl acetate. The resultant was separated and washed with water twice, and then with a saturated saline once. An organic layer was dried over magnesium sulfate, and it was then filtered. The filtrate was concentrated under a reduced pressure. The residue was purified by silica gel column chromatography (developing solvent; ethyl acetate:hexane=1:40). The obtained mixture was subjected to azeotropy with benzene 2 times, and it was then dissolved in 29 mL (100 mM) of DMF. 2.28 mg (7.3 mmol) of tetrabutylammonium fluoride trihydrate was added to the above solution, and the obtained mixture was stirred at 0° C. After stirring for 15 minutes, after confirming the termination of the reaction by TLC, the reaction solution was neutralized with a saturated ammonium chloride aqueous solution. This reaction solution was washed with water twice, and then with a saturated saline once. An organic layer was dried over magnesium sulfate, and was then filtered. The filtrate was concentrated under a reduced pressure. The residue was purified by silica gel column chromatography (developing solvent; ethyl acetate:hexane=1:4→ethyl acetate:methanol: water=20:2:1) to obtain Boc-Thr(S-SsecBu) of interest (yield amount: 650 mg, yield percentage: 69%).

SEQUENCE LISTING FREE TEXT

SEQ ID NO: 1 is an amino acid sequence having a protecting group of Example 1.

SEQ ID NO: 2 is an acetylated amino acid sequence of Example 1.
SEQ ID NO: 3 is an amino acid sequence having methylated cysteine of Example 1.
SEQ ID NO: 4 is an acetylated amino acid sequence of Example 1.
SEQ ID NO: 5 is an amino acid sequence having a protecting group of Example 2.
SEQ ID NO: 6 is an amino acid sequence of Example 2.
SEQ ID NO: 7 is an amino acid sequence having methylated cysteine of Example 2.
SEQ ID NO: 8 is an amino acid sequence of Example 2.
SEQ ID NO: 9 is an amino acid sequence having a protecting group of Example 3.
SEQ ID NO: 10 is an amino acid sequence of Example 3.
SEQ ID NO: 11 is an amino acid sequence having methylated cysteine of Example 3.
SEQ ID NO: 12 is an amino acid sequence of Example 3.
SEQ ID NO: 13 is a sugar chain-added amino acid sequence having a protecting group of Example 4.
SEQ ID NO: 14 is a sugar chain-added amino acid sequence having a protecting group of Example 4.
SEQ ID NO: 15 is a sugar chain-added amino acid sequence having a benzylthioester group of Example 4.
SEQ ID NO: 16 is an amino acid sequence having a protecting group of Example 4.
SEQ ID NO: 17 is an amino acid sequence of Example 4.
SEQ ID NO: 18 is a sugar chain-added amino acid sequence of Example 4.
SEQ ID NO: 19 is a sugar chain-added amino acid sequence having methylated cysteine of Example 4.
SEQ ID NO: 20 is a sugar chain-added amino acid sequence of Example 4.
SEQ ID NO: 21 is an amino acid sequence having a protecting group and methionine sulfoxide of Example 5.
SEQ ID NO: 22 is an acetylated amino acid sequence having methionine sulfoxide of Example 5.
SEQ ID NO: 23 is an acetylated amino acid sequence having methylated cysteine and methionine sulfoxide of Example 5.
SEQ ID NO: 24 is an acetylated amino acid sequence of Example 5.
SEQ ID NO: 25 is an amino acid sequence having a protecting group of Example 6.
SEQ ID NO: 26 is a sugar chain-added amino acid sequence having a protecting group of Example 6.
SEQ ID NO: 27 is a sugar chain-added amino acid sequence having a protecting group of Example 6.
SEQ ID NO: 28 is a sugar chain-added amino acid sequence having a benzylthioester group of Example 6.
SEQ ID NO: 29 is a sugar chain-added amino acid sequence of Example 6.
SEQ ID NO: 30 is a sugar chain-added amino acid sequence of Example 6.
SEQ ID NO: 31 is a sugar chain-added amino acid sequence having methylated cysteine of Example 6.
SEQ ID NO: 32 is a sugar chain-added amino acid sequence of Example 6.
SEQ ID NO: 33 is an amino acid sequence having a protecting group of Example 7.
SEQ ID NO: 34 is an amino acid sequence having a benzylthioester group of Example 7.
SEQ ID NO: 35 is an amino acid sequence having a protecting group and a threonine derivative of Example 7.
SEQ ID NO: 36 is an amino acid sequence having a threonine derivative of Example 7.
SEQ ID NO: 37 is an amino acid sequence having a threonine derivative of Example 7.
SEQ ID NO: 38 is an amino acid sequence having a threonine derivative of Example 7.
SEQ ID NO: 39 is an amino acid sequence of Example 7.

INDUSTRIAL APPLICABILITY

The present invention provides a method for producing a peptide and a glycopeptide. According to the present invention, even in a case in which a peptide that does not contain cysteine is to be obtained, a ligation method can be applied. In addition, the present invention is also useful for the production of an N-linked glycopeptide and an O-linked glycopeptide.

The invention claimed is:

1. A method for producing a peptide comprising an amino acid residue having an —OH group, comprising converting an —SH group of a peptide comprising an amino acid residue having the —SH group to the —OH group, wherein said method comprises the following steps (a) to (c):
  (a) allowing the —SH group in a peptide to react with a methylating agent to convert the —SH group to an -SMe group;
  (b) allowing the -SMe group obtained in the step (a) to react with a cyanizing agent; and
  (c) modifying the reaction conditions to become more basic than the conditions in the step (b) to achieve a pH between pH 9 and pH 13.

2. The method for producing a peptide according to claim 1, wherein the amino acid residue having the —SH group is a cysteine residue, the —SH group of the cysteine residue in the peptide reacts with the methylating agent in the step (a), and the cysteine residue is converted to a serine residue by converting the —SH group to the —OH group.

3. A method for producing a peptide comprising an amino acid residue having an —OH group, comprising converting an -SMe group of a peptide comprising an amino acid residue having the -SMe group to the —OH group, wherein said method comprises the following steps (b) and (c):
  (b) allowing the -SMe group in the peptide to react with a cyanizing agent to produce a reaction intermediate; and
  (c) converting the reaction intermediate obtained in the step (b) to the peptide comprising an amino acid residue having an —OH group under more basic conditions than the conditions in the step (b) to achieve a pH between pH 9 and pH 13.

4. The method for producing a peptide according to claim 1, wherein the peptide comprising an amino acid residue having the —SH group further comprises a methionine residue, wherein the methionine residue in the peptide is a protected methionine residue, and the production method further comprises the following step (d) after the step (b) or (c), as desired:
  (d) deprotecting the protected methionine residue.

5. The method for producing a peptide according to claim 1, wherein the production method further comprises the following step (o) before the step (a), and the —SH group in the peptide obtained in the step (o) reacts with the methylating agent in the step (a):
  (o) ligating a first peptide containing, at the C-terminus thereof, an amino acid residue in which a carboxyl group is substituted with a thioester group represented by the formula —C(=O)—SR (wherein R is selected from a benzyl group, an aryl group, and an alkyl group, which may be substituted with substituents), to a second peptide containing, at the N-terminus thereof, an amino acid residue having an —SH group according to a ligation method to obtain the peptide comprising an amino acid residue having the —SH group.

6. The method for producing a peptide according to claim 2, wherein the production method further comprises the following step (o) before the step (a), and the —SH group of the cysteine in the peptide obtained in the step (o) reacts with a methylating agent in the step (a):
  (o) ligating a first peptide containing, at the C-terminus thereof, an amino acid residue in which a carboxyl group is substituted with a thioester group represented by the formula —C(=O)—SR (wherein R is selected from a benzyl group, an aryl group, and an alkyl group, which may be substituted with substituents), to a second peptide containing, at the N-terminus thereof, a cysteine residue according to a ligation method to obtain a peptide comprising a cysteine residue.

7. The method for producing a peptide according to claim 5, wherein said first peptide is a peptide that does not contain a cysteine residue, or a peptide that contains a protected cysteine residue, and said second peptide is a peptide that does not contain a cysteine residue in any regions other than the N-terminus thereof, or a peptide whose cysteine residues in regions other than the N-terminus thereof are all protected cysteine residues.

8. The method for producing a peptide according to claim 1, wherein the peptide comprising an amino acid residue having the —SH group is a glycopeptide, and a glycopeptide comprising an amino acid residue having the —OH group is obtained.

9. The method for producing a peptide according to claim 8, wherein the glycopeptide has an N-linked sugar chain.

10. The method for producing a peptide according to claim 8, wherein the amino acid residue having the —SH group is a cysteine residue, and the production method further comprises the following step (o) before the step (a), and the —SH group of the cysteine residue in the glycopeptide obtained in the step (o) reacts with the methylating agent in the step (a):
  (o) ligating a first glycopeptide whose C-terminus is represented by the following formula:

-sugar Asn-X—C(=O)—SR (wherein sugar Asn represents a sugar chain-added asparagine,
  X represents a portion other than a carboxyl group of any given amino acid residue other than proline, and R is selected from a benzyl group, an aryl group, and an alkyl group, which may be substituted with substituents), to a second peptide containing a cysteine residue at the N-terminus thereof according to a ligation method to obtain a glycopeptide containing a cysteine residue.

11. The method for producing a peptide according to claim 3, wherein the peptide comprising an amino acid residue having the -SMe group further comprises a methionine residue, wherein the methionine residue in the peptide is a protected methionine residue, and the production method further comprises the following step (d) after the step (b) or (c), as desired:

(d) deprotecting the protected methionine residue.

12. A method for producing a peptide comprising an amino acid residue having an —OH group, comprising: converting an —SH group of a peptide comprising an amino acid residue having the —SH group to the —OH group, wherein said method comprises the following steps (a) to (c):
   (a) allowing the —SH group in a peptide to react with a methylating agent to convert the —SH group to an -SMe group;
   (b) allowing the -SMe group obtained in the step (a) to react with a cyanizing agent; and
   (c) modifying the reaction conditions to become more basic than the conditions in the step (b) by adding an amount of hydrazine hydrate sufficient to achieve a pH between pH 10 and pH 11.

* * * * *

SEQUENCE LISTING

```
<160> NUMBER OF SEQ ID NOS: 39

<210> SEQ ID NO 1
<211> LENGTH: 4
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Ala having blocking group Fmoc
<220> FEATURE:
<221> NAME/KEY: MOD_RES
<222> LOCATION: (2)..(2)
<223> OTHER INFORMATION: Cys having blocking group Trt

<400> SEQUENCE: 1

Ala Cys Gly Leu
1

<210> SEQ ID NO 2
<211> LENGTH: 4
<212> TYPE: PRT
<213> ORGANISM: artificial sequence
```

```
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION

<400> SEQUENCE: 2

Ala Cys Gly Leu
1

<210> SEQ ID NO 3
<211> LENGTH: 4
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: METHYLATION

<400> SEQUENCE: 3

Ala Cys Gly Leu
1

<210> SEQ ID NO 4
<211> LENGTH: 4
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION

<400> SEQUENCE: 4

Ala Ser Gly Leu
1

<210> SEQ ID NO 5
<211> LENGTH: 8
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Val having blocking group Fmoc
<220> FEATURE:
<221> NAME/KEY: MOD_RES
<222> LOCATION: (2)..(2)
<223> OTHER INFORMATION: Asp having blocking group OtBu
<220> FEATURE:
<221> NAME/KEY: MOD_RES
<222> LOCATION: (3)..(3)
<223> OTHER INFORMATION: Lys having blocking group Boc
<220> FEATURE:
<221> NAME/KEY: MOD_RES
<222> LOCATION: (6)..(6)
<223> OTHER INFORMATION: Cys having blocking group Trt

<400> SEQUENCE: 5

Val Asp Lys Ala Val Cys Gly Leu
1               5
```

```
<210> SEQ ID NO 6
<211> LENGTH: 8
<212> TYPE: PRT
<213> ORGANISM: artificial sequence
<220> FEATURE:
<223> OTHER INFORMATION: synthetic construct

<400> SEQUENCE: 6

Val Asp Lys Ala Val Cys Gly Leu
1               5

<210> SEQ ID NO 7
<211> LENGTH: 8
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (6)..(6)
<223> OTHER INFORMATION: METHYLATION

<400> SEQUENCE: 7

Val Asp Lys Ala Val Cys Gly Leu
1               5

<210> SEQ ID NO 8
<211> LENGTH: 8
<212> TYPE: PRT
<213> ORGANISM: artificial sequence
<220> FEATURE:
<223> OTHER INFORMATION: synthetic construct

<400> SEQUENCE: 8

Val Asp Lys Ala Val Ser Gly Leu
1               5

<210> SEQ ID NO 9
<211> LENGTH: 11
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Leu having blocking group Fmoc
<220> FEATURE:
<221> NAME/KEY: MOD_RES
<222> LOCATION: (3)..(3)
<223> OTHER INFORMATION: Arg having blocking group Pbf
<220> FEATURE:
<221> NAME/KEY: MOD_RES
<222> LOCATION: (5)..(5)
<223> OTHER INFORMATION: Tyr having blocking group tBu
<220> FEATURE:
<221> NAME/KEY: MOD_RES
<222> LOCATION: (6)..(6)
<223> OTHER INFORMATION: Cys having blocking group Trt
<220> FEATURE:
<221> NAME/KEY: MOD_RES
<222> LOCATION: (10)..(10)
<223> OTHER INFORMATION: Arg having blocking group Pbf

<400> SEQUENCE: 9

Leu Phe Arg Val Tyr Cys Asn Phe Leu Arg Gly
1               5                   10
```

```
<210> SEQ ID NO 10
<211> LENGTH: 11
<212> TYPE: PRT
<213> ORGANISM: artificial sequence
<220> FEATURE:
<223> OTHER INFORMATION: synthetic construct

<400> SEQUENCE: 10

Leu Phe Arg Val Tyr Cys Asn Phe Leu Arg Gly
1               5                   10

<210> SEQ ID NO 11
<211> LENGTH: 11
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (6)..(6)
<223> OTHER INFORMATION: METHYLATION

<400> SEQUENCE: 11

Leu Phe Arg Val Tyr Cys Asn Phe Leu Arg Gly
1               5                   10

<210> SEQ ID NO 12
<211> LENGTH: 11
<212> TYPE: PRT
<213> ORGANISM: artificial sequence
<220> FEATURE:
<223> OTHER INFORMATION: synthetic construct

<400> SEQUENCE: 12

Leu Phe Arg Val Tyr Ser Asn Phe Leu Arg Gly
1               5                   10

<210> SEQ ID NO 13
<211> LENGTH: 6
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Ala having blocking group Fmoc
<220> FEATURE:
<221> NAME/KEY: CARBOHYD
<222> LOCATION: (5)..(5)
<223> OTHER INFORMATION: Asn glycosylated by asialo oligosaccharide
      chain
<220> FEATURE:
<221> NAME/KEY: MOD_RES
<222> LOCATION: (6)..(6)
<223> OTHER INFORMATION: Ser having blocking group tBu

<400> SEQUENCE: 13

Ala Leu Leu Val Asn Ser
1               5

<210> SEQ ID NO 14
<211> LENGTH: 6
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Ala having blocking group Boc
```

```
<220> FEATURE:
<221> NAME/KEY: CARBOHYD
<222> LOCATION: (5)..(5)
<223> OTHER INFORMATION: Asn glycosylated by asialo oligosaccharide
      chain
<220> FEATURE:
<221> NAME/KEY: MOD_RES
<222> LOCATION: (6)..(6)
<223> OTHER INFORMATION: Ser having blocking group tBu

<400> SEQUENCE: 14

Ala Leu Leu Val Asn Ser
1               5

<210> SEQ ID NO 15
<211> LENGTH: 6
<212> TYPE: PRT
<213> ORGANISM: artificial sequence
<220> FEATURE:
<223> OTHER INFORMATION: synthetic construct
<220> FEATURE:
<221> NAME/KEY: CARBOHYD
<222> LOCATION: (5)..(5)
<223> OTHER INFORMATION: Asn glycosylated by asialo oligosaccharide
      chain
<220> FEATURE:
<221> NAME/KEY: MOD_RES
<222> LOCATION: (6)..(6)
<223> OTHER INFORMATION: Ser having benzyl thioester group

<400> SEQUENCE: 15

Ala Leu Leu Val Asn Ser
1               5

<210> SEQ ID NO 16
<211> LENGTH: 14
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Cys having blocking groups Fmoc and Trt
<220> FEATURE:
<221> NAME/KEY: MOD_RES
<222> LOCATION: (4)..(4)
<223> OTHER INFORMATION: Trp having blocking group Boc
<220> FEATURE:
<221> NAME/KEY: MOD_RES
<222> LOCATION: (5)..(5)
<223> OTHER INFORMATION: Glu having blocking group OtBu
<220> FEATURE:
<221> NAME/KEY: MOD_RES
<222> LOCATION: (10)..(10)
<223> OTHER INFORMATION: His having blocking group Trt
<220> FEATURE:
<221> NAME/KEY: MOD_RES
<222> LOCATION: (12)..(12)
<223> OTHER INFORMATION: Asp having blocking group OtBu
<220> FEATURE:
<221> NAME/KEY: MOD_RES
<222> LOCATION: (13)..(13)
<223> OTHER INFORMATION: Lys having blocking group Boc

<400> SEQUENCE: 16

Cys Gln Pro Trp Glu Pro Leu Gln Leu His Val Asp Lys Ala
1               5                   10

<210> SEQ ID NO 17
<211> LENGTH: 14
<212> TYPE: PRT
<213> ORGANISM: artificial sequence
```

```
<220> FEATURE:
<223> OTHER INFORMATION: synthetic construct

<400> SEQUENCE: 17

Cys Gln Pro Trp Glu Pro Leu Gln Leu His Val Asp Lys Ala
1               5                   10

<210> SEQ ID NO 18
<211> LENGTH: 20
<212> TYPE: PRT
<213> ORGANISM: artificial sequence
<220> FEATURE:
<223> OTHER INFORMATION: synthetic construct
<220> FEATURE:
<221> NAME/KEY: CARBOHYD
<222> LOCATION: (5)..(5)
<223> OTHER INFORMATION: Asn glycosylated by asialo oligosaccharide
      chain

<400> SEQUENCE: 18

Ala Leu Leu Val Asn Ser Cys Gln Pro Trp Glu Pro Leu Gln Leu His
1               5                   10                  15

Val Asp Lys Ala
            20

<210> SEQ ID NO 19
<211> LENGTH: 20
<212> TYPE: PRT
<213> ORGANISM: artificial sequence
<220> FEATURE:
<223> OTHER INFORMATION: synthetic construct
<220> FEATURE:
<221> NAME/KEY: CARBOHYD
<222> LOCATION: (5)..(5)
<223> OTHER INFORMATION: Asn glycosylated by asialo oligosaccharide
      chain
<220> FEATURE:
<221> NAME/KEY: MOD_RES
<222> LOCATION: (7)..(7)
<223> OTHER INFORMATION: METHYLATION

<400> SEQUENCE: 19

Ala Leu Leu Val Asn Ser Cys Gln Pro Trp Glu Pro Leu Gln Leu His
1               5                   10                  15

Val Asp Lys Ala
            20

<210> SEQ ID NO 20
<211> LENGTH: 20
<212> TYPE: PRT
<213> ORGANISM: artificial sequence
<220> FEATURE:
<223> OTHER INFORMATION: synthetic construct
<220> FEATURE:
<221> NAME/KEY: CARBOHYD
<222> LOCATION: (5)..(5)
<223> OTHER INFORMATION: Asn glycosylated by asialo oligosaccharide
      chain

<400> SEQUENCE: 20

Ala Leu Leu Val Asn Ser Ser Gln Pro Trp Glu Pro Leu Gln Leu His
1               5                   10                  15

Val Asp Lys Ala
            20
```

```
<210> SEQ ID NO 21
<211> LENGTH: 5
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Gly having blocking group Fmoc
<220> FEATURE:
<221> NAME/KEY: MOD_RES
<222> LOCATION: (2)..(2)
<223> OTHER INFORMATION: Cys having blocking group Trt
<220> FEATURE:
<221> NAME/KEY: MOD_RES
<222> LOCATION: (4)..(4)
<223> OTHER INFORMATION: Methionine Sulfoxide

<400> SEQUENCE: 21

Gly Cys Gly Met Ala
1               5

<210> SEQ ID NO 22
<211> LENGTH: 5
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Methionine Sulfoxide

<400> SEQUENCE: 22

Gly Cys Gly Met Ala
1               5

<210> SEQ ID NO 23
<211> LENGTH: 5
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: Methionine Sulfoxide

<400> SEQUENCE: 23

Gly Cys Gly Met Ala
1               5

<210> SEQ ID NO 24
<211> LENGTH: 5
<212> TYPE: PRT
<213> ORGANISM: artificial sequence
<220> FEATURE:
<223> OTHER INFORMATION: synthetic construct
```

```
<220> FEATURE:
<221> NAME/KEY: MOD_RES
<222> LOCATION: (1)..(1)
<223> OTHER INFORMATION: ACETYLATION

<400> SEQUENCE: 24

Gly Ser Gly Met Ala
1               5

<210> SEQ ID NO 25
<211> LENGTH: 18
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Ala having blocking group Fmoc
<220> FEATURE:
<221> NAME/KEY: MOD_RES
<222> LOCATION: (5)..(5)
<223> OTHER INFORMATION: His having blocking group Trt
<220> FEATURE:
<221> NAME/KEY: MOD_RES
<222> LOCATION: (8)..(8)
<223> OTHER INFORMATION: Thr having blocking group tBu
<220> FEATURE:
<221> NAME/KEY: MOD_RES
<222> LOCATION: (9)..(9)
<223> OTHER INFORMATION: Ser having blocking group tBu
<220> FEATURE:
<221> NAME/KEY: MOD_RES
<222> LOCATION: (12)..(12)
<223> OTHER INFORMATION: Asp having blocking group OtBu
<220> FEATURE:
<221> NAME/KEY: MOD_RES
<222> LOCATION: (13)..(13)
<223> OTHER INFORMATION: Thr having blocking group tBu
<220> FEATURE:
<221> NAME/KEY: MOD_RES
<222> LOCATION: (14)..(14)
<223> OTHER INFORMATION: Arg having blocking group Pbf

<400> SEQUENCE: 25

Ala Pro Pro Ala His Gly Val Thr Ser Ala Pro Asp Thr Arg Pro Ala
1               5                   10                  15

Pro Gly

<210> SEQ ID NO 26
<211> LENGTH: 19
<212> TYPE: PRT
<213> ORGANISM: artificial sequence
<220> FEATURE:
<223> OTHER INFORMATION: synthetic construct
<220> FEATURE:
<221> NAME/KEY: CARBOHYD
<222> LOCATION: (1)..(1)
<223> OTHER INFORMATION: Thr glycosylated by N-acetylgalactosamine
<220> FEATURE:
<221> NAME/KEY: MOD_RES
<222> LOCATION: (6)..(6)
<223> OTHER INFORMATION: His having blocking group Trt
<220> FEATURE:
<221> NAME/KEY: MOD_RES
<222> LOCATION: (9)..(9)
<223> OTHER INFORMATION: Thr having blocking group tBu
<220> FEATURE:
<221> NAME/KEY: MOD_RES
<222> LOCATION: (10)..(10)
<223> OTHER INFORMATION: Ser having blocking group tBu
```

```
<220> FEATURE:
<221> NAME/KEY: MOD_RES
<222> LOCATION: (13)..(13)
<223> OTHER INFORMATION: Asp having blocking group OtBu
<220> FEATURE:
<221> NAME/KEY: MOD_RES
<222> LOCATION: (14)..(14)
<223> OTHER INFORMATION: Thr having blocking group tBu
<220> FEATURE:
<221> NAME/KEY: MOD_RES
<222> LOCATION: (15)..(15)
<223> OTHER INFORMATION: Arg having blocking group Pbf

<400> SEQUENCE: 26

Thr Ala Pro Pro Ala His Gly Val Thr Ser Ala Pro Asp Thr Arg Pro
1               5                   10                  15

Ala Pro Gly

<210> SEQ ID NO 27
<211> LENGTH: 20
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Ser having blocking groups Boc and tBu
<220> FEATURE:
<221> NAME/KEY: CARBOHYD
<222> LOCATION: (2)..(2)
<223> OTHER INFORMATION: Thr glycosylated by N-acetylgalactosamine
<220> FEATURE:
<221> NAME/KEY: MOD_RES
<222> LOCATION: (7)..(7)
<223> OTHER INFORMATION: His having blocking group Trt
<220> FEATURE:
<221> NAME/KEY: MOD_RES
<222> LOCATION: (10)..(10)
<223> OTHER INFORMATION: Thr having blocking group tBu
<220> FEATURE:
<221> NAME/KEY: MOD_RES
<222> LOCATION: (11)..(11)
<223> OTHER INFORMATION: Ser having blocking group tBu
<220> FEATURE:
<221> NAME/KEY: MOD_RES
<222> LOCATION: (14)..(14)
<223> OTHER INFORMATION: Asp having blocking group OtBu
<220> FEATURE:
<221> NAME/KEY: MOD_RES
<222> LOCATION: (15)..(15)
<223> OTHER INFORMATION: Thr having blocking group tBu
<220> FEATURE:
<221> NAME/KEY: MOD_RES
<222> LOCATION: (16)..(16)
<223> OTHER INFORMATION: Arg having blocking group Pbf

<400> SEQUENCE: 27

Ser Thr Ala Pro Pro Ala His Gly Val Thr Ser Ala Pro Asp Thr Arg
1               5                   10                  15

Pro Ala Pro Gly
            20

<210> SEQ ID NO 28
<211> LENGTH: 20
<212> TYPE: PRT
<213> ORGANISM: artificial sequence
<220> FEATURE:
<223> OTHER INFORMATION: synthetic construct
<220> FEATURE:
<221> NAME/KEY: CARBOHYD
<222> LOCATION: (2)..(2)
<223> OTHER INFORMATION: Thr glycosylated by N-acetylgalactosamine
```

```
<220> FEATURE:
<221> NAME/KEY: MOD_RES
<222> LOCATION: (20)..(20)
<223> OTHER INFORMATION: Gly having benzyl thioester group

<400> SEQUENCE: 28

Ser Thr Ala Pro Pro Ala His Gly Val Thr Ser Ala Pro Asp Thr Arg
1               5                   10                  15

Pro Ala Pro Gly
            20

<210> SEQ ID NO 29
<211> LENGTH: 20
<212> TYPE: PRT
<213> ORGANISM: artificial sequence
<220> FEATURE:
<223> OTHER INFORMATION: synthetic construct
<220> FEATURE:
<221> NAME/KEY: CARBOHYD
<222> LOCATION: (2)..(2)
<223> OTHER INFORMATION: Thr glycosylated by N-acetylgalactosamine

<400> SEQUENCE: 29

Cys Thr Ala Pro Pro Ala His Gly Val Thr Ser Ala Pro Asp Thr Arg
1               5                   10                  15

Pro Ala Pro Gly
            20

<210> SEQ ID NO 30
<211> LENGTH: 40
<212> TYPE: PRT
<213> ORGANISM: artificial sequence
<220> FEATURE:
<223> OTHER INFORMATION: synthetic construct
<220> FEATURE:
<221> NAME/KEY: CARBOHYD
<222> LOCATION: (2)..(2)
<223> OTHER INFORMATION: Thr glycosylated by N-acetylgalactosamine
<220> FEATURE:
<221> NAME/KEY: CARBOHYD
<222> LOCATION: (22)..(22)
<223> OTHER INFORMATION: Thr glycosylated by N-acetylgalactosamine

<400> SEQUENCE: 30

Ser Thr Ala Pro Pro Ala His Gly Val Thr Ser Ala Pro Asp Thr Arg
1               5                   10                  15

Pro Ala Pro Gly Cys Thr Ala Pro Pro Ala His Gly Val Thr Ser Ala
            20                  25                  30

Pro Asp Thr Arg  Pro Ala Pro Gly
            35                  40

<210> SEQ ID NO 31
<211> LENGTH: 40
<212> TYPE: PRT
<213> ORGANISM: artificial sequence
<220> FEATURE:
<223> OTHER INFORMATION: synthetic construct
<220> FEATURE:
<221> NAME/KEY: CARBOHYD
<222> LOCATION: (2)..(2)
<223> OTHER INFORMATION: Thr glycosylated by N-acetylgalactosamine
<220> FEATURE:
<221> NAME/KEY: MOD_RES
<222> LOCATION: (21)..(21)
<223> OTHER INFORMATION: METHYLATION
<220> FEATURE:
<221> NAME/KEY: CARBOHYD
<222> LOCATION: (22)..(22)
<223> OTHER INFORMATION: Thr glycosylated by N-acetylgalactosamine
```

```
<400> SEQUENCE: 31

Ser Thr Ala Pro Pro Ala His Gly Val Thr Ser Ala Pro Asp Thr Arg
1               5                   10                  15

Pro Ala Pro Gly Cys Thr Ala Pro Pro Ala His Gly Val Thr Ser Ala
            20                  25                  30

Pro Asp Thr Arg  Pro Ala Pro Gly
        35               40

<210> SEQ ID NO 32
<211> LENGTH: 40
<212> TYPE: PRT
<213> ORGANISM: artificial sequence
<220> FEATURE:
<223> OTHER INFORMATION: synthetic construct
<220> FEATURE:
<221> NAME/KEY: CARBOHYD
<222> LOCATION: (2)..(2)
<223> OTHER INFORMATION: Thr glycosylated by N-acetylgalactosamine
<220> FEATURE:
<221> NAME/KEY: CARBOHYD
<222> LOCATION: (22)..(22)
<223> OTHER INFORMATION: Thr glycosylated by N-acetylgalactosamine

<400> SEQUENCE: 32

Ser Thr Ala Pro Pro Ala His Gly Val Thr Ser Ala Pro Asp Thr Arg
1               5                   10                  15

Pro Ala Pro Gly Ser Thr Ala Pro Pro Ala His Gly Val Thr Ser Ala
            20                  25                  30

Pro Asp Thr Arg  Pro Ala Pro Gly
        35               40

<210> SEQ ID NO 33
<211> LENGTH: 4
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glu having blocking groups Boc and OtBu
<220> FEATURE:
<221> NAME/KEY: MOD_RES
<222> LOCATION: (2)..(2)
<223> OTHER INFORMATION: Ser having blocking group tBu

<400> SEQUENCE: 33

Glu Ser Asn Gly
1

<210> SEQ ID NO 34
<211> LENGTH: 4
<212> TYPE: PRT
<213> ORGANISM: artificial sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: Gly having benzyl thioester group

<400> SEQUENCE: 34

Glu Ser Asn Gly
1
```

```
<210> SEQ ID NO 35
<211> LENGTH: 4
<212> TYPE: PRT
<213> ORGANISM: artificial sequence
<220> FEATURE:
<223> OTHER INFORMATION: synthetic construct
<220> FEATURE:
<221> NAME/KEY: MUTAGEN
<222> LOCATION: (1)..(1)
<223> OTHER INFORMATION: Thr derivative having S-SsecBu group in place
      of hydroxy group and blocking group Boc
<220> FEATURE:
<221> NAME/KEY: MOD_RES
<222> LOCATION: (3)..(3)
<223> OTHER INFORMATION: Thr having blocking group tBu

<400> SEQUENCE: 35

Xaa Leu Thr Leu
1

<210> SEQ ID NO 36
<211> LENGTH: 4
<212> TYPE: PRT
<213> ORGANISM: artificial sequence
<220> FEATURE:
<223> OTHER INFORMATION: synthetic construct
<220> FEATURE:
<221> NAME/KEY: MUTAGEN
<222> LOCATION: (1)..(1)
<223> OTHER INFORMATION: Thr derivative having S-SsecBu group in place
      of hydroxy group

<400> SEQUENCE: 36

Xaa Leu Thr Leu
1

<210> SEQ ID NO 37
<211> LENGTH: 8
<212> TYPE: PRT
<213> ORGANISM: artificial sequence
<220> FEATURE:
<223> OTHER INFORMATION: synthetic construct
<220> FEATURE:
<221> NAME/KEY: MUTAGEN
<222> LOCATION: (5)..(5)
<223> OTHER INFORMATION: Thr derivative having thiol group in place of
      hydroxy group

<400> SEQUENCE: 37

Glu Ser Asn Gly Xaa Leu Thr Leu
1               5

<210> SEQ ID NO 38
<211> LENGTH: 8
<212> TYPE: PRT
<213> ORGANISM: artificial sequence
<220> FEATURE:
<223> OTHER INFORMATION: synthetic construct
<220> FEATURE:
<221> NAME/KEY: MUTAGEN
<222> LOCATION: (5)..(5)
<223> OTHER INFORMATION: Thr derivative having methylated thiol group in
      place of hydroxy group

<400> SEQUENCE: 38

Glu Ser Asn Gly Xaa Leu Thr Leu
1               5
```

-continued

```
<210> SEQ ID NO 39
<211> LENGTH: 8
<212> TYPE: PRT
<213> ORGANISM: artificial sequence
<220> FEATURE:
<223> OTHER INFORMATION: synthetic construct

<400> SEQUENCE: 39

Glu Ser Asn Gly Thr Leu Thr Leu
1               5
```